United States Patent [19]

Gala et al.

[11] Patent Number: 4,863,918
[45] Date of Patent: Sep. 5, 1989

[54] ENAMINE QUATERNARY COMPOUNDS, METHODS OF MAKING AND THEIR USE AS MUSCLE RELAXANTS

[75] Inventors: Kanti J. Gala, Union; Ross C. Terrell, Clark, both of N.J.

[73] Assignee: BOC, Inc., New Providence, N.J.

[21] Appl. No.: 221,141

[22] Filed: Jul. 19, 1988

Related U.S. Application Data

[63] Continuation-in-part of Ser. No. 11,942, Feb. 6, 1987, abandoned.

[51] Int. Cl.$^4$ .................. A61K 31/395; C07D 491/22
[52] U.S. Cl. ..................... 514/213; 514/255; 514/343; 514/235.5; 546/15; 546/78; 546/192; 546/150; 546/348; 544/230; 544/106; 544/403; 544/70; 548/409; 540/594
[58] Field of Search ............ 546/15, 18; 544/70, 544/230; 548/409; 514/213, 225, 255, 343

[56] References Cited

U.S. PATENT DOCUMENTS

| | | | |
|---|---|---|---|
| 3,424,755 | 1/1969 | Aenss et al. | 546/19 |
| 3,669,986 | 6/1972 | Porter | 546/15 |
| 3,839,273 | 11/1974 | Murayama et al. | 546/18 |
| 3,899,464 | 8/1975 | Murayama et al. | 546/18 |
| 3,992,390 | 11/1976 | Holt et al. | 546/222 |
| 4,016,168 | 4/1977 | Murayama et al. | 546/19 |
| 4,021,432 | 5/1977 | Holt et al. | 546/16 |
| 4,096,114 | 6/1978 | Minagawa et al. | 546/19 |
| 4,097,587 | 6/1978 | Soma et al. | 546/215 |
| 4,125,533 | 11/1978 | Marayama et al. | 546/19 |
| 4,141,883 | 2/1979 | Soma et al. | 546/16 |
| 4,173,599 | 11/1979 | Minagawa et al. | 546/19 |
| 4,212,974 | 7/1980 | Murayama et al. | 546/19 |
| 4,222,931 | 9/1980 | Minagawa et al. | 546/18 |
| 4,237,294 | 12/1982 | Somd et al. | 546/19 |
| 4,265,803 | 5/1981 | Somd et al. | 546/19 |
| 4,289,686 | 9/1981 | Rody et al. | 546/19 |
| 4,319,030 | 9/1982 | Weizer et al. | 546/19 |
| 4,323,684 | 4/1982 | Kubata et al. | 546/19 |
| 4,336,183 | 6/1982 | Nakahara et al. | 546/19 |
| 4,340,534 | 7/1982 | Weizer et al. | 546/19 |

OTHER PUBLICATIONS

Leonard, et al., "Unsaturated Amines XIII" 2/5/59, J. Am. Chem. Soc., pp. 595–602 vol. 81 (1959).

Rice, et al., "Amides of 3,9-Dicarboxy-2,4,8,10-Tetraoxaspiro [5.5]Undecane", 9/65, pp. 704–705, J. Med. Chem., vol. 8 (1965).

Clements, et al., "Some 3,9-Dicarboxylic Acids of 2,4,8,10-Tetraoxaspiro[5.5]Undecane", 12/59, pp. 1958–1961, J. Org. Chem., vol. 24 (1959).

Usov, V. A., et al., "Synthetic Route to Acetals of Enamino Ketone Via Methanolysis of 4-(3-Methoxy--etc." 1987 (Abstract).

*Primary Examiner*—Robert T. Bond
*Attorney, Agent or Firm*—R. Hain Swope; Larry R. Cassett

[57] ABSTRACT

Disclosed are novel enamine quaternary compounds of the formula

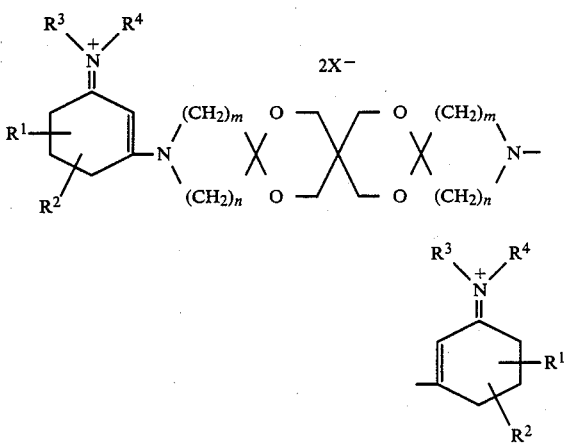

wherein m=1, 2 or 3 and n=1, 2 or 3 with the proviso that m+n=3, 4 or 5; $R^1$ and $R^2$ are independently lower alkyl or hydrogen, and $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkyloyloxy lower alkyl or wherein $NR^3R^4$ together comprise a heterocycle ring; and wherein $X^-$ represents a pharmaceutically acceptable anion. Pharmaceutical compositions containing the same when administered to warm-blooded animals exhibit a muscle relaxant effect characterized by excellent onset and recovery times. Also disclosed are methods of making the enamine quaternary compounds.

30 Claims, No Drawings

ENAMINE QUATERNARY COMPOUNDS, METHODS OF MAKING AND THEIR USE AS MUSCLE RELAXANTS

FIELD OF THE INVENTION

The present invention is directed to novel enamine quaternary compounds, to pharmaceutical compositions containing the same which are useful as muscle relaxants and to methods of making such compounds.

BACKGROUND OF THE INVENTION

Muscle relaxant drugs are known to affect the transmission of nerve impulses to muscle fibers by either (a) blocking the acetylcholine induced depolarization of the post junctional membrane of the myoneural unit (i.e., a non-depolarizing muscle relaxant) or (b) promoting and prolonging depolarization to prevent the return of the myoneural unit to the resting state and thereby render the muscle refractory to nerve impulse (i.e., a depolarizing muscle relaxant). *Structural Forms of Anesthetic Compounds.* Hugh S. Mathewson, M.D. (Charles C. Thomas, 1961).

Depolarizing muscle relaxants such as succinylcholine have the major disadvantage that they are not easily reversed by anticholinesterase drugs.

Non-depolarizing agents such as d-tubocurarine and pancuronium are known to have certain drawbacks which limit their effectiveness as muscle relaxants. For example, they maintain paralysis for an undesirably long time and the recovery period is slow. It is not uncommon for anticholinesterase agents such as neostigmine and edrophonium to be employed to antagonize the effects of such muscle relaxants. A further disadvantage of non-depolarizers is that they can cause side-effects such as bradycardia, tachycardia, hypotension, and hypertension and must therefore be carefully administered and controlled.

Applicant has discovered a novel class of compounds described hereinafter which exhibit potent muscle relaxing activity of the non-depolarizing type while exhibiting desirable onset, duration and recovery times. Comparatively less changes in hemodynamic parameters (heart rate, arterial pressure, myocardial contractility and cardiac output) are produced by compounds of the present invention.

It is an object of the present invention to provide novel enamine quaternary compounds which are useful as muscle relaxants.

It is another object of the invention to provide pharmaceutical compositions containing the novel compounds which when administered to warm-blooded animals exhibit muscle relaxing activity.

It is a further object of the invention to provide methods of making the novel enamine quaternary compounds.

It is a further object to provide enamine quaternary intermediates which are valuable building blocks for making novel enamine quaternary muscle relaxants.

SUMMARY OF THE INVENTION

The present invention is directed to novel enamine quaternary compounds having the formula:

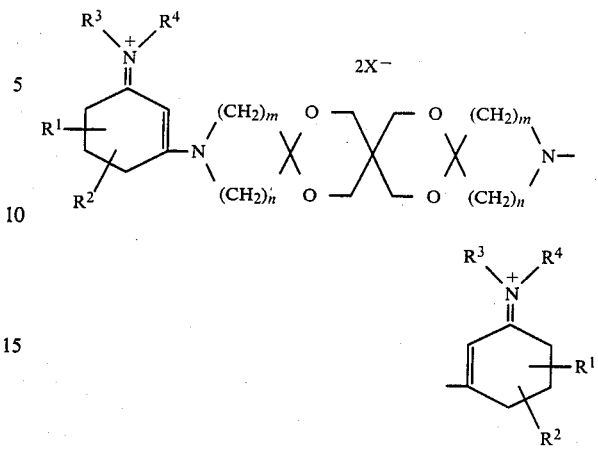

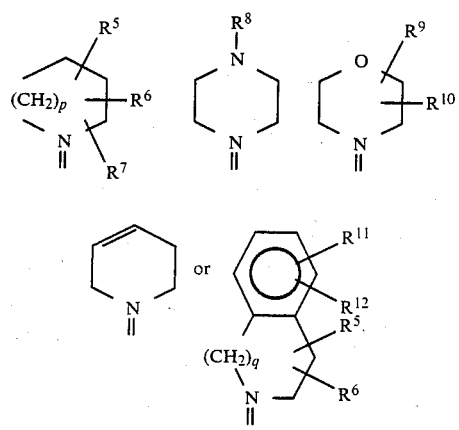

wherein $m=1$, 2 or 3 and $n=1$, 2 or 3 with the proviso that $m+n=3$, 4 or 5; $R^1$ and $R^2$ are independently lower alkyl or hydrogen, $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkyloyloxy lower alkyl or wherein $NR^3R^4$ together comprise a heterocyclic ring selected from the group consisting of wherein P is 1, 2 or 3 and q is 1 or 2 and $R^5$, $R^6$, and $R^7$ are independently hydrogen, hydroxy lower alkyl, lower alkoxy phenyl, phenyl lower alkyl wherein the phenyl is unsubstituted or substituted with up to 2 lower alkoxy groups or $R^5$ and $R^6$ combined is a lower alkyl bridge or $R^5$ and $R^6$ together are a lower ketal or lower acetal moiety; $R^8$ is lower alkyl or diphenylmethylene wherein the phenyl may be unsubstituted or substituted by a halogen; $R^9$ and $R^{10}$ are independently selected from lower alkyl and hydrogen; $R^{11}$ and $R^{12}$ are on the same or different carbons and independently are hydrogen, lower alkyl or lower alkoxy; and wherein $X^-$ represents a pharmaceutically acceptable anion such as for example, halides, sulfates, methane sulfonate, benzene sulfonate, nitrobenzene sulfonate, toluene sulfonate and naphthalene sulfonate. The methyl benzyl sulfonate and bromide salts are preferred in clinical use.

By lower alkyl, lower alkoxy, or "lower" applied in combination with any other group, we mean groups containing from 1 to 7 carbon atoms and preferably 1 to 4 carbon atoms.

The compounds of the present invention have muscle relaxant or neuromuscular blocking properties. They would be indicated for endotrachial intubation and maintenance of surgical relaxation. Many of the compounds provide acceptable potency, rapid onset and recovery and short duration of action. This is particularly desirable for surgical procedures in an out-patient setting where the patient must be street-ready at the earliest possible time. The compounds of the present invention can be used together with a pharmaceutically acceptable carrier to provide pharmaceutical compositions and can be administered to mammals such as man in amounts sufficient to provide neuromuscular blockade or muscle relaxation.

One preferred class of compounds is the same as that described above but wherein $R^3$ and $R^4$ are independently substituted or unsubstituted lower alkyl and lower cycloalkyl lower alkyl.

One preferred class of compounds within the scope of the present invention are of the formula

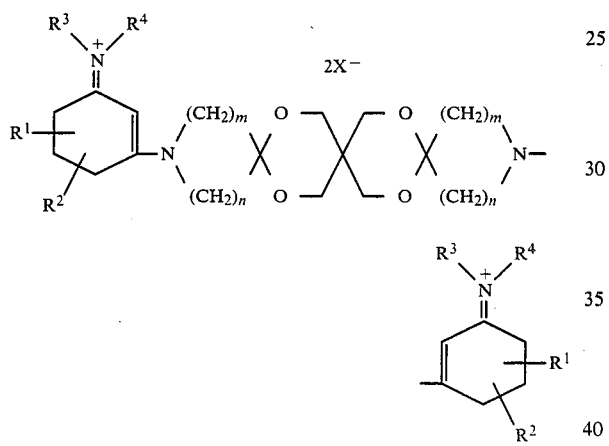

wherein m=1, 2 or 3 and n=1, 2 or 3 with the proviso that m+n=3, 4 or 5; $R^1$ and $R^2$ are independently lower alkyl or hydrogen, $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkyloyloxy lower alkyl and wherein $X^-$ represents a pharmaceutically acceptable anion such as for example, halides, sulfates, methane sulfonate, benzene sulfonate, nitrobenzene sulfonate, toluene sulfonate and naphthalene sulfonate.

Another preferred class of compounds within the scope of this invention is of the formula

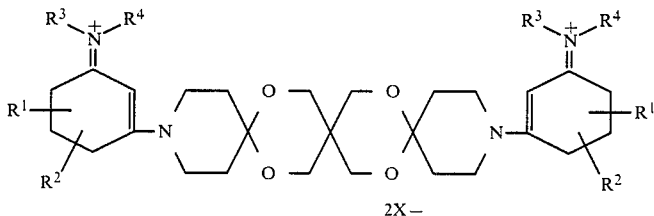

wherein $R^1$ and $R^2$ are independently lower alkyl or hydrogen; $R^3$ and $R^4$ are independently selected from the group consisting of lower alkyl, lower cycloalkyl lower alkyl, lower alkoxy lower alkyl, or lower alkyl substituted with a fluorine.

Intermediates useful in the making of muscle relaxants are also claimed having the following formula

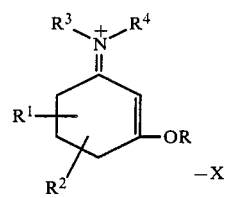

wherein R is a leaving group, e.g. lower alkyl, mesyl, or triflate and $R^1$ and $R^2$ are independently lower alkyl or hydrogen, $R^3$ and $R^4$ are independently selected from the group consisting of lower alkyl, lower cycloalkyl lower alkyl, lower alklenyl, phenyl lower alkyl, thienyl lower alkyl, furyl lower alkyl, lower alkoxy lower alkyl, halogenated lower alkyl, lower alkyloyloxo or lower alkyloyloxy lower alkyl or wherein $NR^3R^4$ together comprise a heterocyclic ring selected from the group consisting of

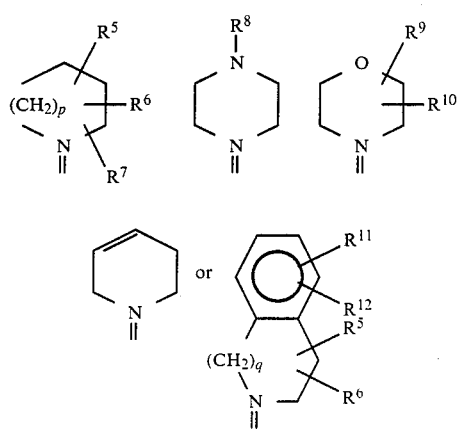

wherein P is 2 or 3 and q is 1 or 2 and $R^5$, $R^6$ and $R^7$ are independently hydrogen, hydroxy lower alkyl, lower alkoxy phenyl, phenyl lower alkyl wherein the phenyl is unsubstituted or substituted with up to 2 lower alkoxy groups or $R^5$ and $R^6$ combined is a lower alkyl bridge or $R^5$ and $R^6$ together are a lower ketal or lower acetal moiety; $R^8$ is lower alkyl or diphenylmethylene wherein the phenyl may be unsubstituted or substituted by a halogen; $R^9$ and $R^{10}$ are independently selected from lower alkyl and hydrogen; $R^{11}$ and $R^{12}$ are on the same or different carbons and independently are hydrogen, lower alkyl or lower alkoxy; and wherein $X^-$ represents a pharmaceutically acceptable anion such as for example, halides, sulfates, methane sulfonate, benzene sulfonate, nitrobenzene sulfonate, toluene sulfonate and naphthalene sulfonate.

One preferred class of intermediates within the scope of the present invention are of the formula

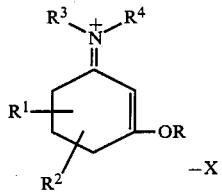

wherein R is a leaving group such as lower alkyl, mesyl, or triflate; $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkloyloxy lower alkyl and wherein $X^-$ represents a pharmaceutically acceptable anion such as for example, halides, sulfates, methane sulfonate, benzene sulfonate, nitrobenzene sulfonate, toluene sulfonate and naphthalene sulfonate.

A preferred class of compounds within the scope of the invention are of the formula

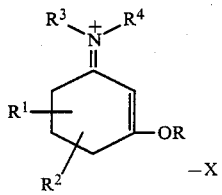

wherein R is as defined above and $R^1$ and $R^2$ are $R^3$ and $R^4$ are independently selected from the group consisting of lower alkyl, lower cycloalkyl lower alkyl, lower alkoxy lower alkyl or lower alkyl substituted with fluorine.

The compounds may be prepared by reacting a mixture of pentaerythritol and the salt (e.g., hydrochloride) of 4,4-dihydroxy piperidone to obtain the salt of a spiro-diamine which is then reacted with a base to obtain a first starting material having the formula:

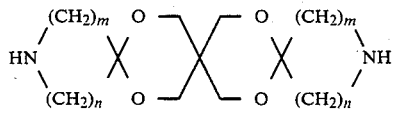

wherein m and n are independently 1, 2 or 3 with the proviso that m+n=3, 4 or 5. The piperidine ring may be substituted with a lower alkyl.

The second starting material is prepared by reacting hexamethyleneimine and 5,5-dimethyl-1,3-cyclohexanedione under gentle heating in the presence of a solvent. The resulting product is reacted with an organic salt (e.g. methyl iodide) to obtain the second starting material having the formula

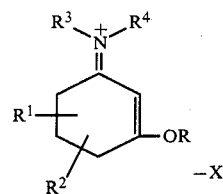

wherein $R^1$, $R^2$, $R^3$ and $R^4$ or $NR^3R^4$ are as defined above.

The first and the second starting materials are reacted in the presence of a solvent to obtain the quaternary iodide salt. This can be converted to a pharmaceutically acceptable anion such as for example methane sulfonate, benzene sulfonate, p-toluene sulfonate, nitrobenzene sulfonate, naphthalene sulfonate and the like by reacting with a corresponding silver salt (e.g. silver p-toluene sulfonate).

Compositions of the present invention may be made by combining the compounds with a suitable liquid carrier for the preparation of an injectable solution. The liquid carriers are those customarily used for injectable solution and include distilled water and saline.

The injectable compositions are prepared so that the effective dosage of the active ingredient is in the range of from about 0.1 to about 7.0 mg/kg, preferably from about 0.15 to about 2.5 mg/kg.

EXAMPLE 1

Spiro-diamine

A mixture of pentaerythritol (13.6 g, 0.1 mol) and 4-4-dihydroxy piperidone hydrochloride (31.2 g, 0.2 mol), both agents commercially available from Aldrich Chemical Co., in the presence of 0.2 g of p-toluenesulfonic acid monohydrate was refluxed in toluene (250 ml) for 24 hours in a Dean-Stark reflux apparatus. After collecting 7 ml of water, the reaction mixture was cooled, and the solvent was decanted. The resulting hydrochloride salt was triturated with methanol and then collected by filtration. (30.5 g, 82% yield). The hydrochloride salt was dissolved in a minimum amount of water (e.g. about 100 ml) and was filtered to remove insoluble material. The filtered product was combined with a 50% aqueous sodium hydroxide solution until a pH of 11 was attained. The resulting solid white product was extracted three times with chloroform (300 ml). The chloroform extracts were combined, washed three times with 50 ml of water, and dried over sodium sulfate. The chloroform was thereafter evaporated leaving a solid product which was thereafter dried, (22 g, 74% yield) to obtain a compound (m.p. 133°–135° C.) having the formula

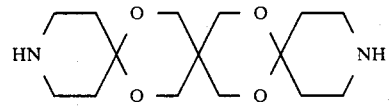

EXAMPLE 2

Enamine

A mixture of cyclohexamethyleneimine (9.91 g, 0.1 mol) and 5,5-dimethyl-1,3-cyclohexanedione (14 g, 0.1 mol), both commercially available from Aldrich Chemical Company, was refluxed in an apparatus containing a Dean-Stark trap to collect water. The reaction mixture was concentrated after the collection of about 0.2 ml of water. The resulting orange colored oil was triturated with petroleum ether (b.p. 30°–60° C.) to obtain (22.1 g) of an enamino ketone. The enamino ketone was dissolved in methyl iodide (30 ml) and refluxed for 48 hours. The solid material was separated and added to 200 ml of ethyl acetate to thereby form a white solid (23.0 g) which recrystallized from methanol/ethyl acetate (17.7 g, 49% yield, m.p. 145°–148° C.) having the formula

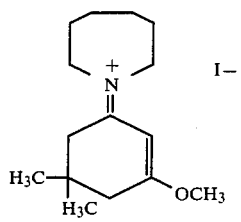

| Analysis Calculated for $C_{15}H_{26}NOI$ | | |
|---|---|---|
| | Theoretical | Calculated |
| C | 49.59 | 49.54 |
| H | 7.16 | 7.21 |
| N | 3.86 | 4.06 |

EXAMPLE 3

Spiro-diamine Enamine

The reaction product of Example 1 in an amount of 1.00 g (0.000335 mol) was dissolved in 5 ml of methanol. A 2.432 g (0.0067 mol) portion of the reaction product of formula Example 2 was added thereto. The reaction mixture was stirred at room temperature for three days and then filtered with the removal of methanol. A powdery residue was thereby obtained which was triturated with ethyl acetate. The resulting yellowish white powdery residue was collected by filtration (3.10 g, 92% yield, m.p. 165°–170° C.) having the formula

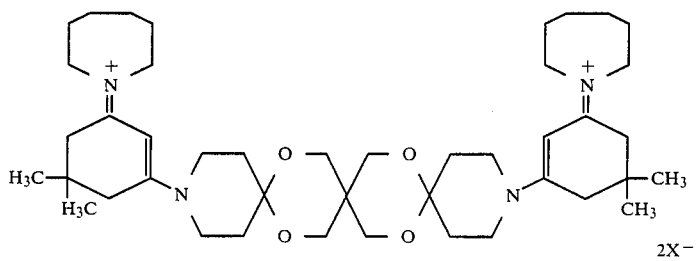

| Analysis Calculated for $C_{43}H_{70}N_4I_2O_4H_2O$ | | |
|---|---|---|
| | Theoretical | Found | Found |
| C | 52.76 | 53.00 | 53.01 |
| H | 7.41 | 7.20 | 7.26 |
| N | 5.72 | 5.81 | 5.86 |

EXAMPLE 4

Toluene Sulfonate Salt

The compound of Example 3 in an amount of 0.495 g was added to 15 ml of methanol. 0.29 g of silver p-toluene sulfonate in 250 ml of methanol was added to the mixture. The resulting reaction mixture was stirred overnight at room temperature. The resulting solid was removed and solvent was evaporated to obtain an oil which was then triturated with ether to obtain a solid product (i.e. a toluene sulfonate salt). (0.170 g, 31% yield, m.p. 81°–86° C.).

| Analysis Calculated for $C_{57}H_{86}N_4S_2O_{10}.3H_2O$ | | |
|---|---|---|
| | Theoretical | Found | Found |
| C | 61.92 | 61.61 | 61.80 |
| H | 8.38 | 7.93 | 8.20 |
| N | 5.06 | 4.88 | 4.68 |

EXAMPLE 5

Spiro-Diamine

A round bottom flask is equipped with a Dean-Stark trap, condenser and heating mantle. The flask is charged with 1-benzyl-3-piperidone hydrochloride hydrate (25 g, 0.11 mol), pentaerythritol (7.53 g, 0.055mol), p-toluene-sulfonic acid (0.05 g, 0.003 mol) and 300 ml toluene. The solution was refluxed for 14 hours and then concentrated to a brown oil. This oil was taken up in water, made basic with ammonia and then extracted into chloroform. The organic layer was washed with brine, dried with sodium sulfate, and evaporated to an oil. The oil was purified by chromatographing on approximately 600 mg silica gel (230–400 mesh) using a step gradient. The first solvent is 80% ethyl acetate, 20% hexane which removes non-polar impurities and the product is eluted with pure ethyl acetate. Two major spots are observed by thin layer chromatography (TLC) on silica plates when eluting with ethyl acetate, the desired product has RF=0.41, the mono-ketal has RF=0.14. After recrystallization from ethyl acetate-hexane, 9.25 g of the desired product is obtained. N-benzyl-3-ketal-trispiro diamine (m.P. 125°–127° C., ca. 30% yield).

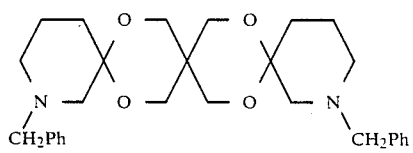

EXAMPLE 6

Debenzylated Spiro-Diamine

All the product from Example 5 is dissolved in 200 ml of warm 1:1 methanol and ethanol. The benzyl compound stays in solution on cooling and is then debenzylated with Pearlman's catalyst. The reaction mixture is treated with 50 psi hydrogen overnight on the Parr shaker and then filtered through glass fiber paper. The clear filtrate is concentrated in vacuo to give a quantitative yield of a clear oil which crystallizes upon standing. This reaction can be monitored by TLC; the starting material has RF=0.7 and the debenzylated product has RF=0.25 when eluted with methylene chloride: methanol 2:8.

EXAMPLE 7

Oxalate Salt of Spiro-diamine

The crude amine from Example 6 is dissolved in about 100 ml chloroform and diluted to approximately 250 ml with ether. A saturated solution of oxalic acid in ether is added; the salt precipitates out immediately. It is filtered and recrystallized by dissolving in methanol and adding water. A quantitative yield is obtained. (Allowing the debenzylated product from Example 6 to stand overnight before making the salt resulted in a decrease in the yield to approximately 60%.) The salt is dried overnight at 0.05 to 0.1 mm Hg, 50° C. (m.p.=235°–237° C.).

| | Analysis Calculated for $C_{15}H_{26}N_2O_4 \cdot (C_4H_8O_4)$ | | |
|---|---|---|---|
| | Theoretical | Found | Found |
| C | (47.69) | 47.70 | 47.72 |
| H | (6.32) | 6.20 | 6.25 |
| N | (5.86) | 6.18 | 6.24 |

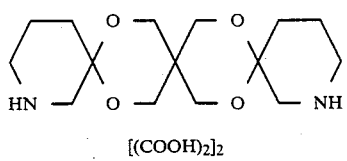

[(COOH)$_2$]$_2$

EXAMPLE 8

Spiro-diamine

N-benzyloxycarbonylperhydroazepin-4-one (13 g, 0.526mol) (See Example 13 for synthesis), pentaerythritol (3.58 g, 0.0263mol), and p-toluenesulfonic acid (500mg) were taken into 300 ml of toluene and refluxed for 16 hours using a Dean-Stark trap. The reaction mixture was concentrated in vacuo to afford a clear yellow oil. This oil was purified on a silica gel column eluting with 7/3 hexane/ethyl acetate. The desired fractions were combined and evaporated to afford a viscous, yellow oil, wt.=13.9 g (88.9%).

| | Analysis Calculated for $C_{33}H_{42}N_2O_8$ | | |
|---|---|---|---|
| | Found | Found | Theoretical |
| C | 66.06, | 65.97 | (66.64) |
| H | 7.16, | 7.12 | (7.12) |

| | Analysis Calculated for $C_{33}H_{42}N_2O_8$ | | |
|---|---|---|---|
| | Found | Found | Theoretical |
| N | 4.78, | 4.71 | (4.71) |

EXAMPLE 9

The N,N-1-dibenzyloxy-trispiro (13.9 g, 0.0234mol) of Example 8 was taken into 50 ml of methanol and connected to a Paar under 50 psi of hydrogen for 16 hours. The reaction mixture was filtered through glass fiber filter paper, and the filtrate was concentrated in vacuo to afford the crude trispiro-diamine (white solid). The diamine was dissolved into 200 ml of isopropanol. A solution of oxalic acid (4.5 g, 0.05 mol) in 200 ml of isopropanol was added to this diamino solution. A white precipitate formed immediately. This solution was heated to near boiling, cooled to room temperature, filtered, and dried to yield 10.6 g (81.7%) of the dioxalate salt (m.p. 174°–177° C.).

| | Analysis Calculated for $C_{25}H_{34}N_2O_{12}$ | |
|---|---|---|
| | Found | Theoretical |
| C | 49.38 | (49.79) |
| H | 6.63 | (6.77) |
| N | 5.65 | (5.53) |

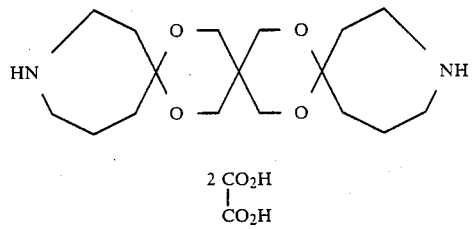

2 CO$_2$H
|
CO$_2$H

EXAMPLE 10

Cyclopropyl Enamino-Ether Quat

N-propylcyclopropanemethylamine (14 g, 0.124 mol) and 5,5-dimethyl-1,3-cyclohexanedione (17.34 g, 0.124 mol) were taken into 350 ml of toluene and refluxed for 16 hours using a Dean Stark trap. The reaction mixture was evaporated in vacuo to afford a red-orange oil. This crude oil was purified on an alumina column eluting with 1:1 ethyl acetate/hexane to afford 22.3 g (76.4%) of the enamino-ketone. The enamino-ketone (22.3 g) was taken into 35 ml of methyl iodide and refluxed for 16 hours whereby a precipitate formed. The reaction was cooled to room temperature and 300 ml of ethyl acetate was added to the reaction mixture. After stirring for 2 hours, the precipitate was filtered and was recrystallized from methanol/ether to afford 11.84 g (33.3%) of the pure ether quat (mp. 148°–149° C.).

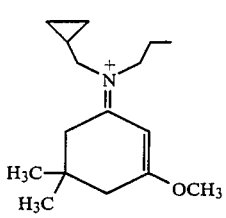

| Analysis Calculated for $C_{16}H_{28}NOI$ | | |
|---|---|---|
| | Found | Found | Theoretical |
| C | 50.92 | 50.89 | (50.93) |
| H: | 7.36 | 7.48 | (7.48) |
| N: | 3.62 | 3.59 | (3.71) |

EXAMPLE 11

Methylpiperidine Enamino-Ether Quat

The compound 3-methylpiperidine (25 g, 0.252 mol) and 5,5-dimethyl- 1,3-cyclohexanedione (35.33 g, 0.252 mol) were taken into 650 ml of toluene and refluxed for 16 hours using a Dean Stark trap. The reaction mixture was concentrated in vacuo to afford a wine red oil. This oil was purified on an alumina column eluting with ethyl acetate. The desired fractions were combined and evaporated in vacuo to afford yellow-orange crystals. The crystalline material was recrystallized from ethyl acetate/petroleum ether to obtain 27.5 g (67.2%) of the pure enamino-ketone. The enamino-ketone (25 g) was refluxed in the presence of 50 ml of methyl iodide for 16 hours. A precipitate formed in the reaction flask. To this reaction mixture was added 200 ml of ethyl acetate and stirred for 2 hours. The crude precipitate was filtered and recrystallized with methanol/ethyl acetate to afford 39.79 g (84%) mp. 148°-149° C.

| Analysis Calculated for $C_{15}H_{26}NOI$ | | |
|---|---|---|
| | Found | Theoretical |
| C | 49.37 | (49.59) |
| H | 7.25 | (7.21) |
| N | 3.73 | (3.86) |

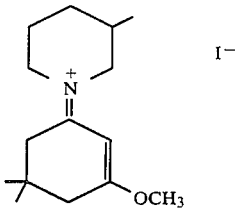

EXAMPLE 12

Enamino Di-Quats

A mixture of the spiro-diamine (0.4 g, 0.0013 mol) prepared according to the method of Example 1 and an enamino ether quat (0.98 g, 0.0026 mol) prepared according to the method of Example 10 were taken into 10 ml of methanol and stirred at room temperature for 48 hours. The solvent was evaporated, and the fluffy material obtained was purified by an alumina column using ethyl acetate as a solvent and then eluting with (EtOAc:MeOH,9:I). The solid obtained was stirred in ethyl acetate, dried and collected (m.p. 125°–131° C.).

| Analysis Calculated for $C_{45}H_{74}N_4O_4I_2$ | | |
|---|---|---|
| | Theoretical | Found | Found |
| C | (54.65) | 54.17 | 54.26 |
| H | (7.54) | 7.20 | 7.79 |
| N | (5.66) | 7.36 | 5.90 |

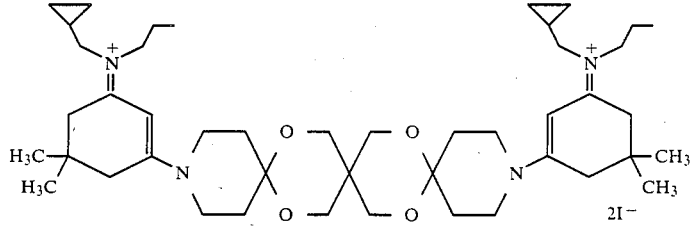

EXAMPLE 13

1-benzyloxycarbonylperhydroazepin $C_{13}H_{15}NO_3$ (i) The compound 4-piperidone hydrochloride monohydrate is recrystallized from ethanol and ether. The recrystallized material is dried at 50° C. at 0.2 mm Hg. Triethylamine (56 ml, 0.4 mol) is added to a suspension of 4-piperidone hydrochloride in 500 ml chloroform. The salt goes into solution immediately. The reaction is stirred at room temperature for 45 minutes and then cooled to 0° C. Dimethyl aminopyridine (600 mg) is added followed by the dropwise addition of benzylchloroformate (28.5 ml, 0.2 mol). The reaction mixture is stirred overnight at room temperature. The reaction is worked up by washing with water (3 times 200 ml), once with brine and then dried with anhydrous sodium sulfate and filtered. The organic phase is concentrated to a yellow oil. Ether is added to the oil; a precipitate forms which is removed by filtration. The filtrate is concentrated to give a clear yellow oil. This oil is further purified by chromatography on silica gel (230 to 400 mesh) using 3:7 ethyl acetate/hexane as eluant. The product is obtained in 75 to 90% yield. See also the method disclosed by Finney, Z. G., Riley, J. N., *J. Med. Chem.*, 23, 895-899 (1980)

| Analysis Calculated for C$_{13}$H$_{15}$NO$_3$ | | |
|---|---|---|
| | Calc | Found | Found |
| C | 66.93 | 66.76 | 66.95 |
| H | 6.48 | 6.72 | 6.71 |
| N | 6.01 | 6.02 | 6.00 |

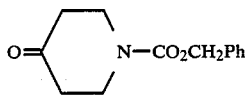

(ii) The benzyloxycarbonylpiperidone (20.3 g, 0.90 mol) is dissolved in 100 ml ether and cooled to −40° C. Boron trifluoride etherate (11.5 ml, 0.092mol in 25 ml ether) and ethyl diazoacetate (12 ml, 0.114mol in 25 ml ether) are then added simultaneously. After the addition, the reaction mixture is kept at 25° C. for one hour, then warmed to room temperature. Then 250 ml of 80% potassium carbonate is added slowly to the reaction mixture. The ether layer is collected, dried with sodium sulfate, and filtered, then concentrated to give the keto-ester as a clear yellow oil (28.5 g).

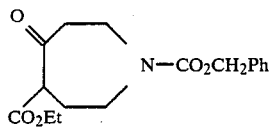

(iii) The keto-ester (31 g, 0.097 mol) sodium chloride (6.25 g, 0.107 mol), and water (6 ml, 0.33 mol) are taken into 45 ml dimethyl sulfate and heated at 180° C. for 48 hours. The reaction is then cooled, diluted with 200 ml water, and extracted three times with 150 ml ether. The combined ether extracts were dried over sodium sulfate, filtered, and concentrated in vacuo to afford 23.3 g of crude product. This product can be purified by distillation (b.p.=178°-180° C. at 0.03 mm Hg) or by column chromatography on silica. The eluant for chromatography is 2:8 ethyl acetate/hexane followed by 3:7 ethyl acetate/hexane. A yield of 50% is obtained.

| Analysis Calculated for C$_{14}$H$_{17}$NO$_3$ | | |
|---|---|---|
| Calc | Found | Found |
| 67.99 | 67.89 | 67.77 |
| 6.93 | 7.19 | 5.50 |

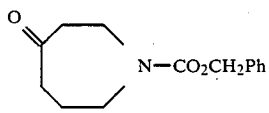

EXAMPLE 14

Synthesis of Enamino-Quat I 36.24 g of amine (3,4-dimethoxy-phenethylamine) and 24.04 of styrene oxcide were taken together and heated at 110-120 degrees Celcius for 18 hours. The reaction mixture was washed with petroleum ether, which was decanted off, and a yellow crystalline material formed. This was purified by passing through a column of silica gel eluting with 50% ethyl acetate/50% hexane initially and increasing the polarity of the system to 80% ethyl acetate/20% hexane until the spot of least polarity was removed for the column. The system was then modified to 90% acetate/10% hexane and finally 100% ethyl acetate until the two spots leading the desired compound were removed from the column. 90% ethyl acetate/10% methanol and 85% ethyl acetate/15% methanol were then used to elute the desired material which was isolated, weight 19.2 (31.9%), melting point 94°-95° C. 9.7 g of the amino alcohol formed was added in portions of 65 ml of cold (0° C.) concentrated sulfuric acid. After the addition, the reaction mixture was stirred for one hour. The reaction mixture was then poured over 500 ml of ice and water and made basic (pH 10) using 50% sodium hydroxide solution. The basic solution was then extracted three times with ether (250 ml per extraction with stirring for fifteen minutes before separation). The ether extracts were dried over anhydrous sodium sulfate and evaporated yielding a yellow oil. This was dissolved in 400 ml of methylene chloride, washed with 100 ml of water, 100 ml of brine, and dried over anhydrous sodium sulfate. The drying agent was removed by filtering and the solvent was evaporated to give a yellow oil. 7.1 g of compound (77.9%) was recovered whose structure was verified by NMR. The secondary amine (7.4 g) was added to 3.7 g of 5,5-dimethyl-1,3-cyclohexane-dione and 300 ml of benzene which was refluxed using a Dean-Stark apparatus. The reaction mixture was concentrated in vacuo to afford a red oil. The crude oil was purified by passing through a column of alumina eluting initially with 70% ethyl acetate/30% hexane and switching to 95% ethyl acetate/5% methanol. The desired fractions were combined to yield 7.52 g (72%) of the enamino ketone compound.

The enaminoketone was dissolved in 18 ml of methyl iodide which was refluxed overnight. A precipitate formed in the vessel. The reaction was cooled to room temperature and 150 ml of ethyl acetate was added and the reaction was stirred at room temperature for three hours. The crude precipitate was filtered, washed well with ethyl acetate and recrystallized from methanol/ether to afford 6.84 g (68.3%) of the following pure compound. (melting point 140-143 degrees Celsius)

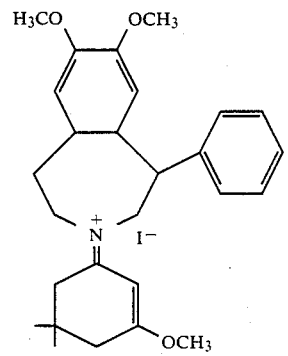

| C, H, N | Calculated | Found |
| --- | --- | --- |
| % C | 59.23 | 59.22 |
| % H | 6.26 | 6.40 |
| % N | 2.56 | 2.70 |

EXAMPLE 15

Synthesis of Enamino-Quat II 22.16 of N-benzyl-3-piperidone hydrochloride monohydrate, 8.7 g of ethylene glycol, and 500mg of p-toluene sulfonic acid monohydrate were taken into 300 ml of toluene and refluxed using a Dean-Stark trap. The reaction mixture was evaporated in vacuo to afford a brown oil. The crude oil was taken into 200 ml of water and 100 ml of chloroform and made alkaline with ammonium hydroxide. The chloroform extracts were combined and washed with brine, then dried over anhydrous sodium sulfate. Removal of the drying agent followed by evaporation at reduced pressure afforded a brown crude oil which was purified on a column of silica gel eluted with 50% ethyl acetate/50% hexane to yield 10.8 g (46.4%) of the ketal. The ketal was then taken into 50 ml of ethanol. To the ethanolic solution was added 900 mg of Pearlman's catalyst (palladium hydroxide on activated carbon). The reaction mixture was connected to the Paar hydrogenator under 50psi of hydrogen Debenzylation was complete after 14 hours at which time the product was filtered through a microfiber filter paper and the catalyst was washed well with ethanol. The mother liquor was evaporated in vacuo to yield 4.45 g (69.1%) of a clear, slightly yellow oil. NMR analysis verified the structure of the product. The secondary amine and 4.36 g of 5,5-dimethyl-1,3-cyclohexanedione were taken into 150 ml of toluene and refluxed using a Dean-Stark apparatus. The reaction mixture was cooled to room temperature and a precipitate formed. The precipitate was filtered and washed with toluene to afford a crude yellow solid. The mother liquor was concentrated in vacuo to afford an orange-red solid. This crude solid was purified on a column of alumina eluting with ethyl acetate. The fractions were combined and evaporated to yield an orange solid. This was washed with hexane, then filtered and combined with the original precipitate and recrystallized from ethyl acetate/hexane to yield 5.5 g (66.7%) of orange crystals of the enaminoketone. The enaminoketone was taken into 15 ml of methyl iodide and refluxed overnight (1ml of acetonitrile was added to bring the enaminoketone into solution). A precipitate formed, 70 ml of ethyl acetate was added and stirring continued at room temperature for four hours. The crude solid was recrystallized from acetonitrile/ethyl acetate to yield a white solid, 6.25 g (76.2%), melting point 154°–156° C., of the following compound.

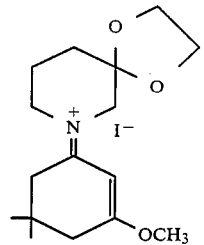

| C, H, N | Calculated | Found |
| --- | --- | --- |
| % C | 47.18 | 47.46, 47.29 |
| % H | 6.44 | 6.21, 6.42 |
| % N | 3.44 | 3.67, 3.57 |

EXAMPLE 16

Synthesis of Enamino-Quat III 18.18 g of N-methylbenzylamine, 15 g of cyclopropylmethyl chloride, 40 g of potassium carbonate, and 12 g of potassium iodide were taken into 300 ml of acetonitrile and refluxed for three days. The reaction was then cooled to room temperature and the inorganic salts were removed by filtration. The filtrate was then evaporated, taken into 500m of methylene chloride, washed twice with 200 ml of water, dried over anhydrous sodium sulfate, and evaporated to afford a clear yellow liquid. The product was distilled at 182°–186° Celsius at greater than 5 mm Hg affording 19.6 g (74%). The structure of the product was verified by NMR. The tertiary amine was debenzylated by dissolving in 50 m of methanol in the presence of 1.5 g of 10% Pd/C and under 50 psi of hydrogen. The reaction mixture was filtered and the filtrate was distilled to afford 6 g of N-methyl-cyclopropylmethyl amine This was taken into 250 ml of benzene and refluxed with 10.7 g of 5,5-dimethyl-1,3-cyclohexanedione using a Dean-Stark trap. The reaction mixture was evaporated in vacuo, then purified on a column of alumina eluting with 50% ethyl acetate/50% hexane. The desired fractions were combined and evaporated to yield 10.45 g (72%) of a yellow oil. NMR verified the structure of the product. The enaminoketone was taken into 15 ml of methyl iodide and refluxed for 6 hours (a precipitate formed after two hours). The reaction mixture was cooled to room temperature and 150 ml of ethyl acetate was added and stirring continued at room temperature overnight. The reaction mixture was filtered and washed with ethyl acetate to afford a white solid. The crude product was recrystallized from methanol/ethyl acetate to yield 8.23 g (46.8%; melting point 153°–155° Celsius) of the following compound.

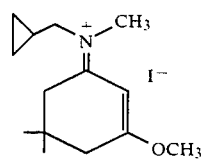

| C, H, N | Calculated | Found |
|---|---|---|
| % C | 48.14 | 48.03 |
| % H | 6.93 | 6.86 |
| % N | 4.01 | 3.84 |

EXAMPLE 17

Synthesis of Enamino-Quat IV 10 g of cyclopropylmethyl chloride, 19.33 g of N-benzylglycine ethyl ester, 27.0 g of potassium carbonate and 8 g of Potassium iodide were taken into 250 ml of acetonitrile and refluxed for 2½ days. The mixture was cooled to room temperature, then filtered to remove the inorganic salts. The filtrate was evaporated in vacuo, taken into 600 ml of chloroform and washed twice with 150 ml portions of water, once with brine, and dried over anhydrous sodium sulfate. The drying agent was removed by filtration and the solvent was evaporated to yield a clear orange liquid. This crude product was purified by passing through silica gel eluting with 95% hexane/5% ethyl acetate. The desired fractions were combined and concentrated to yield the crude amine which was distilled at 158° C./0.25 mm Hg to afford 20.46 g (82.7%) of the following compound

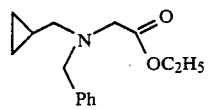

The structure of the product was verified by NMR as follows (values in ppm relative to tetramethylsilane at 0.00 pPm): 7.3 (s,5H aromatic); 4.2 (g, 2H, COCH$_2$); 3.85 (s, 2H, NCH$_2$CO); 3.45 (s, 2H, NCH$_2$Ph); 2.55 (d, 2H, NCH$_2$ *cyclopropyl); 1.3 (t, 3H, COCH$_2$CH$_3$*); 0.1–0.6 (m, 5H, cyclopropyl). The product was debenzylated by dissolving it in 75 ml of methanol in the presence of 2 g of 10% palladium on activated carbon under 51 psi of hydrogen. The reaction was filtered through glass micro fiber filter and the filtrate evaporated to afford a clear liquid Purification was effected by distillation at 132° C. at >5 mmHg to yield 10.75 g (82.7%) of product. The secondary amine and 9.6 g of 5,5-dimethyl-1,3-cyclohexanedione were taken into 250 ml of benzene and refluxed using a Dean-Stark trap Upon completion, the solvent was evaporated to yield a dark red oil. This crude oil was purified by passing through an alumina column eluting with 50% hexane/50% ethyl acetate. The desired enamineketone was collected and evaporated to yield 7.43 g (40%) of an orange oil having the following structure:

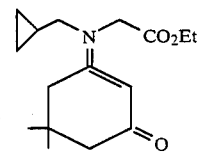

IR analysis structurally verified the ester (1740 cm$^{-1}$) and the conjugated ketone (1610 cm$^{-1}$). The enaminoketone was dissolved in 10 ml of methyliodide and refluxed overnight. The reaction mixture was cooled and 200 ml of ethyl acetate was added and stirring continued for three hours. A white solid was isolated by filtration and recrystallized from methanol/ethyl acetate (yield 5.15; 46% melting point 138°–140° C.) and had the following structure:

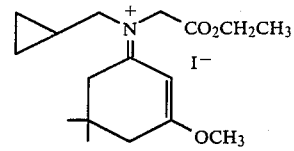

| C, H, N | Calculated | Found |
|---|---|---|
| % C | 48.46 | 47.94, 48.15 |
| % H | 6.69 | 6.51, 6.56 |
| % N | 3.33 | 3.26, 3.43 |

EXAMPLE 18

Synthesis of Enamino-Quat V 20 g of N-benzyloxyperhydroazepin-4-one, 7.54 g of ethylene glycol and 800 mg of p-toluenesulfonic acid monohydrate were taken into 300 ml of toluene and refluxed overnight using a Dean-Stark trap. The reaction mixture was cooled and the solvent was removed under reduced pressure. The crude oil was purified on a column of silica gel eluting with 70% hexane/30% ethyl acetate to afford 17.71 g (75.2%) of the ketal. 17.2 g of the ketal was dissolved in 50 ml of methanol. To this solution was added 1.35 g of Pearlman's catalyst (palladium hydroxide on carbon). The mixture was attached to a hydrogenator at 50 psi overnight. The reaction mixture was filtered and evaporated to afford 9.4 g (86%) of the product. NMR analysis verified the proposed structure.

The product was further reacted by taking it into 150 ml of benzene, adding 7.54 g of 5-methyl-1,3-cyclohexanedione and refluxing the system with a Dean-Stark trap overnight. The solvent was removed under reduced pressure to afford an orange oil. The crude oil was purified on a column of alumina eluting with ethyl acetate to afford 10 g (63%) of the pure enaminoketone whose proposed structure was confirmed by NMR.

The enaminoketone was taken into 10 ml of methyl iodide and refluxed overnight. The reaction mixture was cooled to room temperature, ethyl acetate was added and stirring continued at room temperature for three hours. The crude product was filtered and recrystallized from acetonitrile/ethyl acetate to afford 9 g (58.6%) of the desired product. (melting point 133°–135° C.)

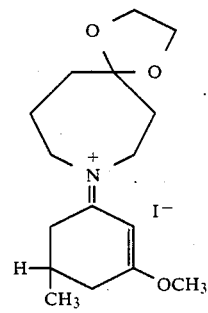

| C, H, N | Calculated | Found |
|---|---|---|
| % C | 47.18 | 46.40, 46.40 |
| % H | 6.43 | 6.26, 6.02 |
| % N | 3.44 | 3.22, 3.29 |

EXAMPLE 19

Enamino-Quat VI

Cyclopropylmethylamine (13 ml; 0.1mol), triethylamine (23 ml; 0.165mol) and 4-Dimethylaminopyridine (500 mg) were taken into 300 ml of chloroform. This solution was cooled to 0° C. and a solution of cyclopropane carboxylic acid chloride (17.25 g; 0.165 mol) in 25 ml of chloroform was added dropwise. The reaction mixture was warmed to room temperature and stirred overnight. The reaction mixture was washed with 200 ml of water, 150 ml of 1N HCl, 200 ml of water and 150 ml of brine. The organic layer was dried over anhydrous sodium sulfate and evaporated under reduced pressure to afford a clear oil which crystallized at room temperature. The crude crystalline material was recrystallized by ethyl acetate/hexane to yield 15.62 g (75%), melting point 65°-67° C., of the following structure:

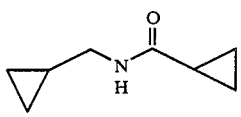

| C, H, N | Calculated | Found |
|---|---|---|
| % C | 69.03 | 69.23 |
| % H | 9.41 | 9.41 |
| % N | 10.06 | 9.93 |

13.2 g of the product previously described was dissolved in 150 ml of anhydrous tetrahydrofuran. This solution was added by metal lines to a solution of lithium aluminum hydride (15 g) in 400 ml of anhydrous tetrahydrofuran. The reaction mixture was refluxed for 18 hours. The reaction was cooled to 0° C. and neutralized with dropwise additions of 10 ml of water, 15 ml of 10% NaOH, and 15 ml of water. The reaction mixture was stirred overnight and filtered to remove the inorganic salts. The filtrate was evaporated to yield 13.5 g of the crude amine. This was purified by vacuum distillation (80° C. at $\geq$ 5 mm Hg) to afford 9.3 g of the pure compound (78.2%). The bis (cyclopropanemethyl) amine and 10.1 g of 5,5-dimethyl-1,3-cyclohexanedione were dissolved in 300 ml of benzene and refluxed using a Dean-Stark trap for 5 days. The solvent was removed at reduced pressure yielding a red orange oil. This was purified through an alumina column eluting with 70% hexane/30% ethyl acetate. A second column was employed in order to obtain the enaminoketone product, 9.1 g (51%). The enaminoketone was taken into 15 ml of methyl iodide and refluxed overnight. A precipitate formed and the mixture was cooled to room temperature. Ethyl acetate was added and the mixture was stirred for several hours. The precipitate was collected by filtration and recrystallized from methanol/ethyl acetate to afford 6.29 g (44.0%) of the quaternized amine of the following structure:

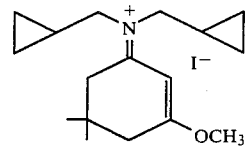

EXAMPLE 20

Synthesis of Enamino-Quat VII 10 g of N-benzyl-3-methyl-4-piperidone hydrochloride, 2.85 g of ethylene glycol and 500 mg of p-toluenesulfonic acid were taken into 300 ml of toluene and refluxed using a Dean-Stark apparatus to remove the water formed.

Upon completion, the reaction mixture was concentrated in vacuo to afford a dark red viscous oil. This oil was taken into 200 ml of methylene chloride and 200 ml of water and basified using ammonium hydroxide. The organic layer was washed once with water, once with brine, dried over anhydrous sodium sulfate and filtered. The solvent was removed under reduced pressure to afford 11 g of a dark red oil. This was purified on a column of silica gel eluting with 80% hexane/20% ethyl acetate affording 6.5 g (63.1%) of the ketal.

The ketal was taken into 75 ml of ethanol. To this solution was added 800 mg of Pearlman's catalyst. The mixture was connected to a hydrogenator at 53 psi of hydrogen. When debenzylation was complete, the reaction mixture was filtered through a microfiber filter paper. The mother liquor was concentrated in vacuo to yield 3.9 g (96%) of a clear oil.

The debenzylation product and 3.4 g of 5,5-dimethy-1,3-cyclohexanedione were taken into 150 ml of toluene and refluxed using a Dean-Stark trap. The solvent was removed at reduced pressure to yield an orange oil which crystallized under vacuum. The crude crystalline material was stirred in hexane for 48 hours and then filtered yielding 5.6 g of product. The product was purified on a column of alumina eluting with ethyl acetate/hexane (1:1) to afford 4 g (60%) of the pure enaminoketone.

The enaminoketone was taken into 12 ml of methyl iodide and refluxed overnight. A precipitate formed in the reaction vessel. The mixture was cooled to room temperature and 150 ml of ethyl acetate was added to the reaction mixture and stirred for two hours. The crude product was filtered, washed well with ethyl acetate and recrystallized from acetonitrile/ethyl acetate to form 4.54 g (77.2%) of pure compound (melting point 163°-165° Celsius) having the following structure:

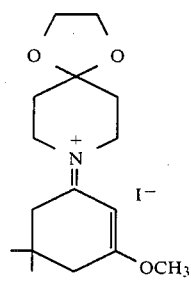

| C, H, N | Calculated | Found |
|---|---|---|
| % C | 48.46 | 48.36 |
| % H | 6.69 | 6.48 |
| % N | 3.33 | 3.23 |

EXAMPLE 21

Enamino-Quat VIII 15 g of cyclopropylmethyl chloride, 20.28 g of N-ethyl benzyl amine, 40 g of potassium carbonate and 12 g potassium iodide were taken into 300 ml of acetonitrile d refluxed for three days. The reaction mixture was cooled to room temperature and filtered to remove the inorganic salts. The mother liquor was evaporated and the residue was taken into 500 ml of chloroform. The mixture was washed twice with 150 ml portions of water, once with brine, dried over anhydrous sodium sulfate, filtered and evaporated to yield 40 g of crude product. This was distilled at 205° C./0.1 mm Hg to afford 28.2 g (100%) of pure compound. The tertiary amine was debenzylated by dissolving it in methanol, adding 2.5 g of Pearlman's catalyst (palladium hydroxide on carbon) and attaching the flask to a Paar hydrogenator at 51 psi of hydrogen. Debenzylation proceeded slowly; therefore, the solution was filtered and 2 g of 10% palladium on carbon was added and hydrogenation was resumed. When thin layer chromatography analysis revealed no starting material the solution was filtered and the filtrate was evaporated to afford a clear, colorless liquid which yielded 12 g of product (81.2%) upon distillation having the following structure:

The secondary amine (9.7 g) and 5,5-dimethyl-1,3-cyclohexanedione (13.79) were dissolved in benzene and refluxed with a Dean-Stark trap. The mixture was concentrated in vacuo and purified on a column of alumina eluting with 70% hexane/30% ethyl acetate to obtain 10 g (46.1%) of the enaminoketone. The enaminoketone was taken into 10 ml of methyl iodide and refluxed overnight. A precipitate formed, so the reaction was cooled to room temperature, ethyl acetate was added and the reaction stirred for two hours. The precipitate was filtered and recrystallized from methanol/ether to obtain 8 g (48.8%) of pure product (melting point 139°–140° C.), having the following structure:

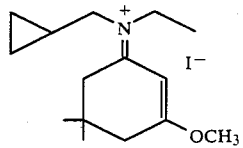

| C, H, N | Calculated | Found |
|---|---|---|
| % C | 49.59 | 49.70 |
| % H | 7.21 | 7.32 |
| % N | 3.86 | 3.65 |

EXAMPLE 22

Enamino-Quat IX 13.5 g of N-ethylbenzylamine, 19.9 g of 2-(2-bromoethyl)-1,3 dioxolane, 8.3 g of potassium iodide, and 41.4 g of potassium carbonate were refluxed in 250 ml of acetonitrile for 2½ days. The reaction mixture was filtered and the filtrate evaporated in vacuo to afford an orange liquid and inorganic salts. This was taken into 40 ml of methylene chloride, filtered through filter paper, and the filtrate was loaded onto a column of silica gel eluting with 90% hexane/10% ethyl acetate, switching to 70% hexane/30% ethyl acetate. The desired fractions were combined and evaporated in vacuo to afford a clear yellow liquid (19.98 g; 84.9%), having the following structure:

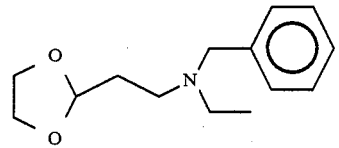

| C, H, N | Calculated | Found |
|---|---|---|
| % C | 71.45 | 71.21 |
| % H | 8.99 | 9.29 |
| % N | 5.95 | 5.76 |

15.1 g of the tertiary amine was taken into 50 ml of methanol. To this was added 1 3 g of 10% palladium on activated carbon. The flask was attached to a Paar hydrogenator at 50 psi of hydrogen. Upon completion of debenzylation, the reaction mixture was filtered through microfiber filter paper. The solvent was evaporated to afford a clear liquid. NMR analysis verified the structure of the product. The crude product was taken into benzene, 9 g of 5,5-dimethyl-1,3-cyclohexanedione was added, and the mixture was refluxed using a Dean-Stark trap. 5.8 g (33.9%) of the enaminoketone was added to 10 ml of methyl iodide and refluxed overnight. The reaction mixture was cooled and ethyl acetate was added. An oil precipitated from the mixture. The solvent was decanted and the crude oil was taken into methanol and the product was recrystallized by addition of ethyl acetate and ether to afford 5.053 g (56.9%) of the desired product, having the following structure:

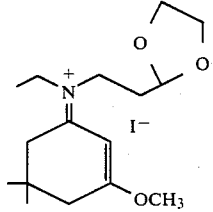

| C, H, N | Calculated | Found |
|---|---|---|
| % C | 46.95 | 46.95 |
| % H | 6.89 | 7.11 |

| C, H, N | Calculated | Found |
|---------|------------|-------|
| % N     | 3.42       | 3.25  |

EXAMPLE 23

In a three neck flask was taken 5 g of sodium hydride (50% dispersion in oil). To this was added 100 ml of anhydrous dimethylformamide. In a 200 ml round bottom flask, 20 g of 1-benzyl-3-hydroxy-4,4-dimethoxypiperidine was dissolved in 100 ml of anhydrous dimethylformamide. This was transferred to the hydride suspension by metal lines and then the reaction was heated to 90° C. for 2.5 hours. After heating, an ice bath was used to cool the flask and 5.2 g of methyl iodide was added by syringe and stirred for 2 days. The solvent was evaporated at reduced pressure and the residue was partitioned between water and ethyl acetate. The organic layer was dried over anhydrous sodium sulfate and evaporated to afford a yellow oil. The product was purified on a column of alumina, eluting with 90% hexane/10% ethyl acetate to yield 16.94 g (80.2%) of the pure compound, as shown by TLC analysis (one spot). This product was further reacted by dissolving it in 40 ml of methanol, 1.5 g of Pearlman's catalyst (palladium hydroxide on carbon) and the starting material was debenzylated under 51 psi of hydrogen in 18 hours. The solution was filtered and the solvent was evaporated to yield 11g (100%) of a clear liquid whose structure was verified by 60 MHz NMR. The secondary amine and 8.8 g of 5,5-dimethyl-1,3-cyclohexanedione were taken into benzene and refluxed using a Dean-Stark trap to remove the resulting water. The reaction mixture was evaporated to afford an orange oil which was purified on a column of alumina eluting with ethyl acetate. The desired fractions were combined and evaporated to afford a clear golden oil which solidified upon standing. The product was recrystallized using ethyl acetate/hexane to afford 9.4 g (50.3%) of the enaminoketone, which was taken into 10 ml of methyl iodide and refluxed for 12 hours. A precipitate formed and the reaction was cooled to room temperature. To the reaction mixture was added 150 ml of ethyl acetate and the reaction was stirred for 2 hours. The crude precipitate was collected by vacuum filtration, washed well with ethyl acetate and recrystallized with methanol/ethyl acetate to afford 8.4 g (60.59) of the pure product (m.p. 137°–138° C.), having the following structure:

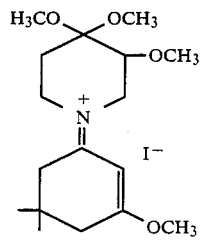

|         | $C_{17}H_{30}NO_4I$ |       |
|---------|---------------------|-------|
| C, H, N | Calculation         | Found |
| % C     | 46.47               | 46.25 |
| % H     | 6.88                | 6.80  |
| % N     | 3.19                | 2.91  |

In accordance with the present invention, similar enamino quat intermediate compounds were synthesized by methods analogous to the above described procedures, as will be readily understood by those skilled in the art. Table I below provides a list of such compounds, which were used as intermediates in preparing the final products of the present invention.

TABLE 1

| No. | Structure | Melting Pt. | Formula | Anal. (C,H,N) | | |
|-----|-----------|-------------|---------|---|---|---|
| 1 | (structure) | 152–156 | $C_{13}H_{22}NOI$ | C<br>H<br>N | 46.72<br>6.50<br>4.25 | (46.57)<br>(6.62)<br>(4.18) |
| 2 | (structure) | 155–156 | $C_{14}H_{24}NOI$ | C<br>H<br>N | 48.13<br>6.90<br>3.95 | (48.18)<br>(6.93)<br>(4.01) |
| 3 | (structure) | 151–153 | $C_{15}H_{26}NOI$ | C<br>H<br>N | 49.74<br>7.19<br>3.83 | (49.59)<br>(7.21)<br>(3.86) |

TABLE 1-continued

| No. | Structure | Melting Pt. | Formula | Anal. (C,H,N) | | |
|---|---|---|---|---|---|---|
| 4 | (structure) | 148–149 | $C_{15}H_{26}NOI$ | C<br>H<br>N | 49.37<br>7.25<br>3.73 | (49.59)<br>(7.21)<br>(3.86) |
| 5 | (structure) | 152–156 | $C_{16}H_{28}NOI$ | C<br>H<br>N | 51.03<br>7.36<br>3.66 | (50.93)<br>(7.48)<br>(3.71) |
| 6 | (structure) | 161–164 | $C_{20}H_{30}NO_4S$ | C<br>H<br>N | 63.25<br>7.67<br>3.59 | (63.24)<br>(7.70)<br>(3.69) |
| 7 | (structure) | 124–125 | $C_{16}H_{28}NOI$ | C<br>H<br>N | 50.96<br>7.58<br>3.88 | (50.93)<br>(7.48)<br>(3.71) |
| 8 | (structure) | 109–110 | $C_{21}H_{30}NOI$ | C<br>H<br>N | 57.04<br>6.88<br>3.33 | (57.40)<br>(6.88)<br>(3.19) |

TABLE 1-continued
| No. | Structure | Melting Pt. | Formula | Anal. (C,H,N) | | |
|---|---|---|---|---|---|---|
| 9 | 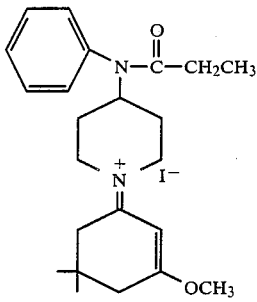 | 158–160 | $C_{23}H_{33}N_2O_2I$ | C 55.68<br>H 6.63<br>N 5.61 | (55.64)<br>(6.69)<br>(5.64) | |
| 10 | 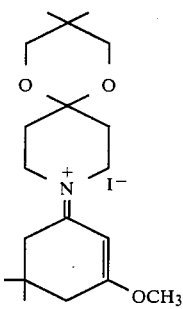 | 165<br>(dec.) | $C_{19}H_{32}NO_3I$ | C 50.96<br>H 7.26<br>N 3.28 | 50.92<br>7.28<br>3.27 | (50.78)<br>(7.18)<br>(3.12) |
| 11 | 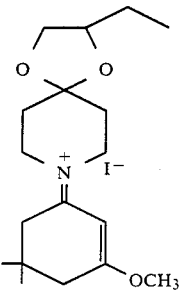 | 155–157 | $C_{18}H_{30}NO_3I$ | C 49.37<br>H 6.95<br>N 3.49 | (49.66)<br>(6.95)<br>(3.22) | |
| 12 | 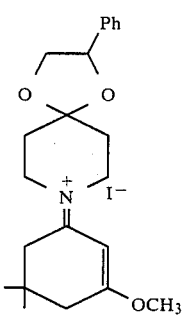 | 161–162 | $C_{22}H_{30}NO_3I$ | C 54.96<br>H 6.31<br>N 3.11 | 54.94<br>6.30<br>3.13 | (54.66)<br>(6.26)<br>(2.90) |
| 13 | 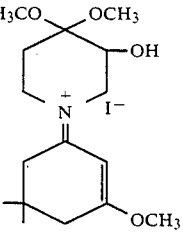 | 174–177 | $C_{16}H_{28}NO_4I$ | C 45.07<br>H 6.45<br>N 3.01 | (45.18)<br>(6.64)<br>(3.29) | |

TABLE 1-continued

| No. | Structure | Melting Pt. | Formula | Anal. (C,H,N) | | | |
|---|---|---|---|---|---|---|---|
| 14 | (structure) | 137–138 | $C_{17}H_{30}NO_4I$ | C<br>H<br>N | 46.25<br>6.80<br>2.91 | | (46.47)<br>(6.88)<br>(3.19) |
| 15 | (structure) | 154–155 | $C_{16}H_{28}NO_3I$ | C<br>H<br>N | 46.80<br>6.70<br>3.68 | | (46.95)<br>(6.89)<br>(3.42) |
| 16 | (structure) | 154–156 | $C_{16}H_{26}NO_3I$ | C<br>H<br>N | 47.46<br>6.21<br>3.67 | 47.29<br>6.42<br>3.57 | (47.18)<br>(6.44)<br>(3.44) |
| 17 | (structure) | 152–154 | $C_{15}H_{24}NO_3I$ | C<br>H<br>N | 45.58<br>5.81<br>3.24 | | (45.81)<br>(6.15)<br>(3.56) |
| 18 | (structure) | 168–170 | $C_{16}H_{26}NO_3I$ | C<br>H<br>N | 47.39<br>6.50<br>3.56 | 47.26<br>6.52<br>3.58 | (47.18)<br>(6.43)<br>(3.44) |
| 19 | (structure) | 163–165 | $C_{17}H_{28}NO_3I$ | C<br>H<br>N | 48.36<br>6.48<br>3.23 | | (48.46)<br>(6.69)<br>(3.33) |

TABLE 1-continued

| No. | Structure | Melting Pt. | Formula | Anal. (C,H,N) | | |
|---|---|---|---|---|---|---|
| 20 | 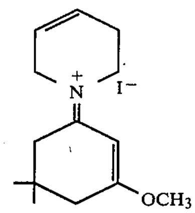 | 144–146 | $C_{14}H_{22}NOI$ | C<br>H<br>N | 48.34<br>6.51<br>3.74 | (48.42)<br>(6.39)<br>(4.03) |
| 21 | 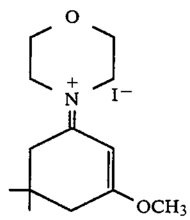 | 166–169 | $C_{13}H_{22}NO_2I$ | C<br>H<br>N | 44.38 44.23<br>6.09 6.19<br>3.96 3.95 | (44.45)<br>(6.31)<br>(3.99) |
| 22 | 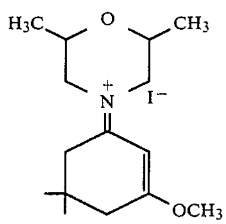 | 152–153 | $C_{15}H_{26}NO_2I$ | C<br>H<br>N | 47.58 47.57<br>6.92 6.94<br>3.91 3.70 | (47.50)<br>(6.91)<br>(3.69) |
| 23 | 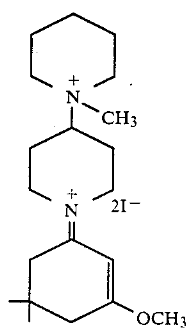 | 227–229 | $C_{20}H_{36}N_2OI_2$ | C<br>H<br>N | 41.15 40.93<br>6.08 6.10<br>4.60 4.50 | (41.80)<br>(6.30)<br>(4.87) |
| 24 | 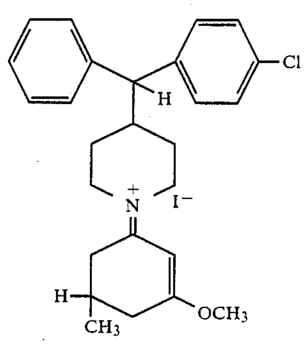 | 157–158 | $C_{26}H_{32}N_2ClOI$ | C<br>H<br>N | 56.43 56.62<br>5.79 5.80<br>4.92 5.14 | (56.68)<br>(5.86)<br>(5.08) |
| 25 | 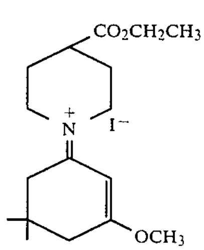 | 145–147 | $C_{17}H_{28}NO_3I$ | C<br>H<br>N | 48.36<br>6.57<br>3.46 | (48.46)<br>(6.70)<br>(3.32) |

TABLE 1-continued

| No. | Structure | Melting Pt. | Formula | Anal. (C,H,N) | | |
|-----|-----------|-------------|---------|---|---|---|
| 26 | 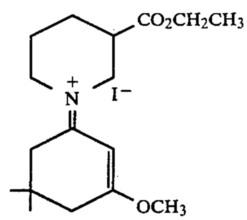 | 132-136 | $C_{17}H_{28}NO_3I$ | C<br>H<br>N | 48.11<br>6.64<br>3.30 | (48.46)<br>(6.70)<br>(3.32) |
| 27 | 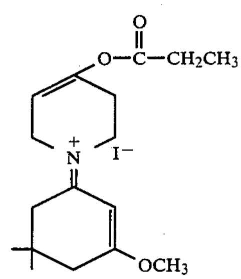 | 155-158 | $C_{17}H_{28}NO_3I$ | C<br>H<br>N | 48.41<br>6.63<br>3.74 | (48.46)<br>(6.70)<br>(3.32) |
| 28 | 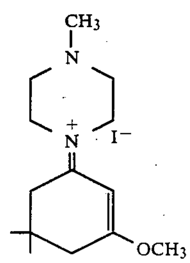 | 259-260 | $C_{14}H_{25}N_2OI$ | C<br>H<br>N | 45.52   45.71<br>6.78   6.84<br>7.85   7.47 | (46.15)<br>(6.91)<br>(7.69) |
| 29 | 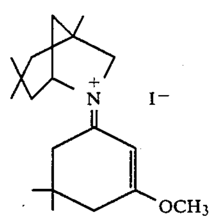 | 155-158 | $C_{19}H_{32}NOI$ | C<br>H<br>N | 54.45<br>7.71<br>3.72 | (54.67)<br>(7.73)<br>(3.36) |
| 30 | 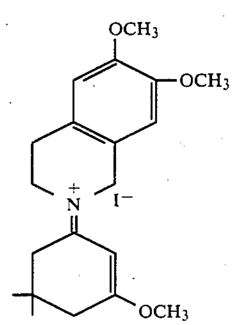 | 175-177 | $C_{20}H_{28}NO_3I$ | C<br>H<br>N | 52.82<br>6.04<br>3.04 | (52.52)<br>(6.17)<br>(3.06) |

TABLE 1-continued

| No. | Structure | Melting Pt. | Formula | Anal. (C,H,N) | | | |
|---|---|---|---|---|---|---|---|
| 31 | (structure) | 209–211, (dec.) | $C_{29}H_{38}NO_5I$ | C<br>H<br>N | 57.38<br>6.19<br>2.30 | 57.15<br>6.20<br>2.26 | (57.33)<br>(6.31)<br>(2.31) |
| 32 | (structure) | 140–143 | $C_{27}H_{34}NO_3I$ | C<br>H<br>N | 59.22<br>6.40<br>2.70 | | (59.23)<br>(6.26)<br>(2.56) |
| 33 | (structure) | 143–145 | $C_{15}H_{26}NOI$ | C<br>H<br>N | 49.59<br>7.14<br>3.96 | 49.34<br>7.09<br>3.88 | (49.59)<br>(7.21)<br>(3.86) |
| 34 | (structure) | 166–167, (dec.) | $C_{18}H_{24}NOI$ | C<br>H<br>N | 54.42<br>6.37<br>3.46 | | (54.41)<br>(6.09)<br>(3.53) |
| 35 | (structure) | 142–144 | $C_{14}H_{24}NOI$ | C<br>H<br>N | 48.27<br>6.68<br>3.98 | | (48.14)<br>(6.93)<br>(4.01) |

TABLE 1-continued

| No. | Structure | Melting Pt. | Formula | Anal. (C,H,N) | | |
|---|---|---|---|---|---|---|
| 36 | 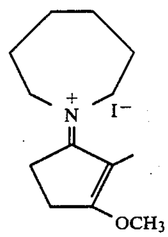 | 110–111 | $C_{13}H_{22}NOI$ | C<br>H<br>N | 46.76<br>6.38<br>4.27 | (46.57)<br>(6.62)<br>(4.18) |
| 37 | 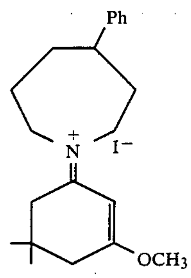 | 132–143 | $C_{21}H_{30}NOI$ | C<br>H<br>N | 57.33<br>6.83<br>3.19 | 57.57 (57.40)<br>6.71 (6.88)<br>3.17 (3.19) |
| 38 | 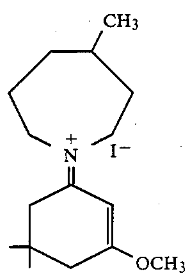 | 119–121 | $C_{16}H_{28}NOI$ | C<br>H<br>N | 50.89<br>7.35<br>4.22 | 50.83 (50.93)<br>7.38 (7.48)<br>4.31 (3.71) |
| 39 | 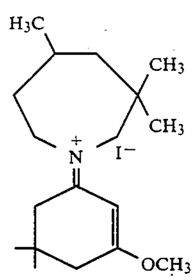 | 132–134,<br>(dec.) | $C_{18}H_{32}NOI$ | C<br>H<br>N | 53.30<br>7.99<br>3.47 | 53.34 (53.33)<br>8.07 (7.96)<br>3.45 (3.46) |
| 40 | 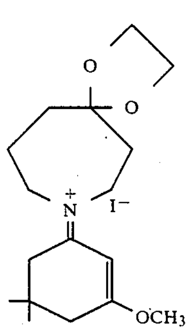 | 134–136 | $C_{17}H_{28}NO_3I$ | C<br>H<br>N | 48.49<br>6.62<br>3.14 | (48.46)<br>(6.69)<br>(3.33) |

TABLE 1-continued

| No. | Structure | Melting Pt. | Formula | Anal. (C,H,N) | | |
|---|---|---|---|---|---|---|
| 41 | 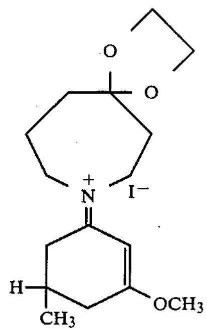 | 133–135 | $C_{16}H_{26}NO_3I$ | C<br>H<br>N | 47.13<br>6.70<br>3.36 | (47.18)<br>(6.43)<br>(3.44) |
| 42 | 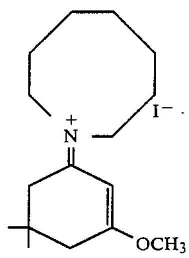 | 122–125 | $C_{16}H_{28}NOI$ | C<br>H<br>N | 50.88<br>7.31<br>3.71 | (50.93)<br>(7.48)<br>(3.71) |
| 43 | 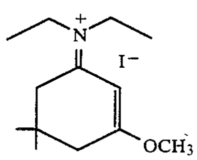 | 135<br>(dec.) | $C_{13}H_{24}NOI$ | C<br>H<br>N | 45.93<br>7.08<br>4.15 | (46.30)<br>(7.17)<br>(4.12) |
| 44 | | 160–162 | $C_{12}H_{22}NOI$ | C<br>H<br>N | 44.29  44.35<br>6.70  6.77<br>4.21  4.22 | (44.59)<br>(6.86)<br>(4.33) | |
| 45 | | 154–157 | $C_{15}H_{28}NOI$ | C<br>H<br>N | 49.41  49.16<br>7.66  7.55<br>4.27  4.23 | (49.32)<br>(7.73)<br>(3.84) | |
| 46 | | 113–115 | $C_{15}H_{24}NOI$ | C<br>H<br>N | 49.99  49.76<br>6.69  6.68<br>4.25  4.13 | (49.87)<br>(6.69)<br>(3.88) | |

TABLE 1-continued

| No. | Structure | Melting Pt. | Formula | Anal. (C,H,N) | | |
|---|---|---|---|---|---|---|
| 47 | 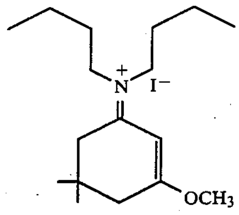 | 155–157 | $C_{17}H_{32}NOI$ | C<br>H<br>N | 52.01<br>8.26<br>3.49 | (51.91)<br>(8.20)<br>(3.56) |
| 48 | 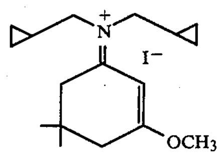 | 145–147 | $C_{17}H_{28}NOI$ | C<br>H<br>N | 52.08<br>7.09<br>3.47 | (52.44)<br>(7.25)<br>(3.59) |
| 49 | 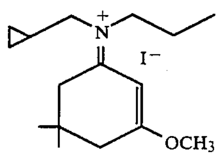 | 148–149 | $C_{16}H_{28}NOI$ | C<br>H<br>N | 50.92 50.89<br>7.36 7.46<br>3.62 3.59 | (50.93)<br>(7.48)<br>(3.71) |
| 50 | 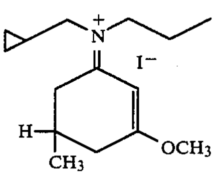 | 158–161 | $C_{15}H_{26}NOI$ | C<br>H<br>N | 49.67<br>7.46<br>3.75 | (49.59)<br>(7.21)<br>(3.86) |
| 51 | 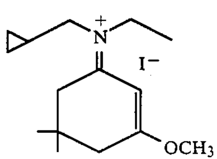 | 139–140 | $C_{15}H_{26}NOI$ | C<br>H<br>N | 49.70<br>7.32<br>3.65 | (49.59)<br>(7.21)<br>(3.86) |
| 52 | 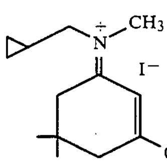 | 153–155 | $C_{14}H_{24}NOI$ | C<br>H<br>N | 48.03<br>6.86<br>3.84 | (48.14)<br>(6.93)<br>(4.01) |
| 53 | 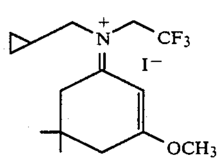 | 138–140 | $C_{15}H_{23}NF_3OI$ | C<br>H<br>N | 43.11<br>5.51<br>3.31 | (43.18)<br>(5.56)<br>(3.36) |
| 54 | 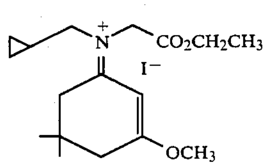 | 138–140 | $C_{17}H_{28}NO_3I$ | C<br>H<br>N | 47.94 48.15<br>6.51 6.56<br>3.26 3.43 | (48.46)<br>(6.69)<br>(3.33) |
| 55 | 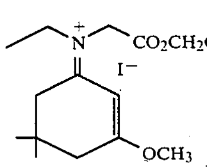 | 130–132 | $C_{15}H_{26}NO_3I$ | C<br>H<br>N | 45.45<br>6.67<br>3.37 | (45.58)<br>(6.63)<br>(3.45) |

TABLE 1-continued

| No. | Structure | Melting Pt. | Formula | Anal. (C,H,N) | | |
|---|---|---|---|---|---|---|
| 56 | H₃C–N⁺(–CH₂CO₂CH₂CH₃) cyclohexenyl-OCH₃, I⁻ | 127–129 | C₁₄H₂₄NO₃I | C<br>H<br>N | 44.31<br>6.12<br>3.65 | (44.10)<br>(6.35)<br>(3.67) |
| 57 | H₃C–N⁺(–CH₂CH₂Ph) cyclohexenyl-OCH₃, I⁻ | 132–133 | C₁₈H₂₆NOI | C<br>H<br>N | 54.04<br>6.56<br>4.06 | 54.05<br>6.50<br>3.90 | (54.14)<br>(6.56)<br>(3.51) |
| 58 | cyclohexylmethyl–N⁺(Et) cyclohexenyl-OCH₃, I⁻ | 138–140 | C₁₈H₃₂NOI | C<br>H<br>N | 53.15<br>7.95<br>3.49 | 53.13<br>8.01<br>3.38 | (53.33)<br>(7.96)<br>(3.46) |
| 59 | Et–N⁺(–CH₂CH₂–dioxolane) cyclohexenyl-OCH₃, I⁻ | 110–113 | C₁₆H₂₈NO₃I | C<br>H<br>N | 46.95<br>7.11<br>3.25 | (46.95)<br>(6.89)<br>(3.42) |
| 60 | Et–N⁺(–CH₂-thienyl) cyclohexenyl-OCH₃, I⁻ | 131–132 | C₁₆H₂₄NOSI | C<br>H<br>N | 47.41<br>5.83<br>3.73 | (47.41)<br>(5.97)<br>(3.46) |
| 61 | (thienyl-CH₂)₂N⁺ cyclohexenyl-OCH₃, I⁻ | 141–143 | C₁₉H₂₄NOS₂I | C<br>H<br>N | 48.47<br>5.19<br>2.71 | (48.19)<br>(5.11)<br>(2.96) |
| 62 | (furyl-CH₂)(thienyl-CH₂)N⁺ cyclohexenyl-OCH₃, I⁻ | 135–137 | C₁₉H₂₄NO₂SI | C<br>H<br>N | 49.89<br>5.24<br>3.14 | 49.76<br>5.22<br>3.26 | (49.89)<br>(5.29)<br>(3.06) |
| 63 | (furyl-CH₂)₂N⁺ cyclohexenyl-OCH₃, I⁻ | 131–133 | C₁₉H₂₄NO₃I | C<br>H<br>N | 51.70<br>5.53<br>2.89 | (51.71)<br>(5.48)<br>(3.17) |

TABLE 1-continued

| No. | Structure | Melting Pt. | Formula | Anal. (C,H,N) | |
|---|---|---|---|---|---|
| 64 | 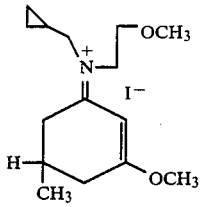 | 138–140 | C₁₅H₂₆NO₂·I | C H N | (47.40) 47.20 (6.90) 6.93 (3.69) 3.61 |

EXAMPLE 24

A compound of the present invention having the structure shown in Example 3 wherein X⁻ is an iodide anion was combined with distilled water to form an injectable solution. Several injectable solutions were prepared having the dosage of the compound set forth in Table I.

Mongrel dogs were injected with 50 mg/kg of pentobarbital until the onset of anesthesia as determined by the eyeblink reflex test. The injectable solutions prepared above were administered intravenously to the anesthesized mongrel dogs and measurements were made of the muscle relaxant effect including maximum twitch depression, onset, duration and recovery time in a clinically known manner. Each of the subjects were compared with a control animal receiving an injection of distilled water. The method was adopted from Ali, H. A. and Savarese, J. J *Anesthesiology*, 45:21–242 (1976), and Savarese, J. J. et al., "The Clinical Pharmacology of High Dose Atracurium", *Anesth. Analg.*, 65:5137 (1986).

As shown by the results of Table II, the compound of the present invention exhibited potent muscle relaxant activity and generally rapid onset and recovery times.

TABLE II

Present Compound in DOGS

|   | Dose (mg/kg) | Max Tw Dep (%) | Max Tw Dep (sec) | Onset (sec) | Duration (min) | Recovery (min) |
|---|---|---|---|---|---|---|
|   | 0.200 | 58 | 225 | 135 | 14.9 | 14.9 |
|   | 0.251 | 87 | 210 | 113 | 15.5 | 11.5 |
| f | 0.316 | 96 | 180 | 100 | 20.2 | 16.0 |
| f | 0.501 | 99 | 165 | 80 | 39.5 | 29.7 |
| f | 0.631 | 100 | 195 | 97 | 28.9 | 18.4 |
|   | 0.794 | 98 | 285 | 162 | 33.3 | 17.8 |
|   | 1.259 | 100 | 120 | 26 | 39.7 | 17.2 |
|   | 1.995 | 100 | 120 | 58 | 50.2 | 26.9 |
|   | 3.162 | 100 | 165 | 43 | 108.9 | 65.9 |
| E | 0.340 | 90 | 205 | 112 | 22.8 | 16.9 | f = female
E = Equi-efficacious does = Dose calculated (using regression analysis) to cause 90% depression to twitch
Max Tw Dep (%) = Percent of maximum (Max) depression (Dep) twitch (TW) from control (e.g. 100% = no twitch) as measured with a force transducer
Max Tw Dep (sec) = Time in seconds to maximum depression of twitch
Onset = Time in seconds to the calculated 85% of the maximum depression of twitch
Train-of-four ratio = Ratio of the amplitude of the fourth twitch to the first in repponse to four electrical pulses (2Hz). Return of the ratio to 75% of control is a clinical index of recovery. Also called T4.
Recovery = Time in minutes from the calculated 100% depression of twitch to return of the train-of-four ratio to the calculated 75% of control.
Duration (min) = time (in minutes) between administration of the drug and the recovery of the T4 to 75%.

EXAMPLE 25

The same compound of the present invention as in 3 was employed to prepare injectable solutions having the dosages shown in Table III. The injectable solutions were administered to New Zealand White rabbits anesthetized in the same manner as the test animals in Example 24. Muscle relaxant activity was determined in the same manner as in Example 24.

As shown in Table III, the composition of the present invention exhibits muscle relaxant potency and brief duration rapid onset and recovery times.

TABLE III

Present Compound in RABBITS

|   | Dose (mg/kg) | Max Tw Dep (%) | Max Tw Dep (sec) | Onset (sec) | Duration (min) | Recovery (min) |
|---|---|---|---|---|---|---|
|   | 0.126 | 40 | 75 | 53 | 3.9 | 3.9 |
|   | 0.158 | 50 | 75 | 39 | 4.1 | 4.1 |
|   | 0.158 | 80 | 135 | 83 | 10.5 | 17.5 |
|   | 0.251 | 95 | 120 | 51 | 9.8 | 7.1 |
|   | 0.251 | 85 | 120 | 64 | 9.7 | 9.4 |
|   | 0.282 | 98 | 165 | 58 | 9.4 | 5.8 |
|   | 0.316 | 93 | 240 | 95 | 10.8 | 5.6 |
|   | 0.316 | 95 | 180 | 58 | 10.2 | 9.5 |
|   | 0.398 | 99 | 105 | 49 | 10.4 | 6.5 |
|   | 0.501 | 96 | 105 | 43 | 10.2 | 7.6 |
|   | 0.631 | 98 | 90 | 36 | 10.7 | 5.2 |
|   | 0.794 | 100 | 240 | 41 | 15.8 | 9.9 |
|   | 1.259 | 99 | 90 | 38 | 20.6 | 8.9 |
|   | 1.995 | 99 | 270 | 44 | 18.4 | 6.6 |
|   | 3.981 | 100 | 45 | 15 | 34.7 | 12.1 |
|   | 7.943 | 100 | 270 | 23 | 68.9 | 23.5 |
| E | 0.240 | 90 | 125 | 56 | 6.6 | 6.0 |

EXAMPLE 26

Evaluation of the compound of Example 12 in rabbits and dogs, in comparison to various standards, revealed a brief duration and rapid onset and recovery. Cardiovascular change were within an acceptable range. The results are shown in Tables IV and V below.

TABLE IV

RABBIT PAW TWITCH EQUI-EFFICACIOUS DOSE DATA

| COMPOUND | DOSE MG/KG | ONSET SEC | RECOV. MIN | DURAT. MIN | HR % | BP % |
|---|---|---|---|---|---|---|
| atracurium | 0.046 | 126.9 | 12.2 | 14.3 | −1.0 | −3.4 |
| BW938 | 0.010 | 282.4 | 101.7 | 167.0 | −3.8 | −5.2 |
| BW1090 | 0.504 | 48.5 | 7.3 | 8.7 | −0.4 | 1.2 |
| conotox. G1 | 0.008 | 367.2 | 52.5 | 73.4 | −0.1 | 3.3 |
| conotox. M1 | 0.010 | 407.1 | 51.3 | 71.9 | 0.5 | 2.8 |
| decamethonium | 0.165 | 104.0 | 41.7* | 41.7* | −2.8 | −2.6 |
| descuronium | 0.053 | 129.4 | 13.1 | 21.5 | −4.1 | −7.6 |
| d-tubocurarine | 0.229 | 85.0 | 34.8 | 37.3 | −0.3 | 4.8 |
| Ex. 12 Compound | 0.209 | 47.7 | 5.8 | 7.1 | 1.0 | 7.3 |
| metocurine | 0.025 | 72.4 | 34.9 | 37.8 | 0.2 | −1.6 |
| pancuronium | 0.022 | 147.5 | 17.4 | 32.5 | 0.0 | 2.7 |
| succinylcholine | 0.447 | 39.4 | 18.6* | 18.6* | 0.2 | −4.1 |
| RGH-4201 | 0.070 | 35.4 | 6.1 | 7.7 | 0.3 | 2.6 |
| vecuronium | 0.019 | 97.3 | 9.6 | 16.8 | −1.9 | 1.1 |

*Since cpd. is a depolarizer, data are based on twitch recovery not t-o-f.

TABLE V

DOG PAW TWITCH EQUI-EFFICACIOUS DOSE DATA

| COMPOUND | DOSE (MG/KG) | ONSET (SEC) | RECOV. (MIN) | DURAT. (MIN) | HR % | BP % |
|---|---|---|---|---|---|---|
| atracurium | 0.086 | 159.4 | 20.4 | 27.9 | 3.3 | 0.3 |
| BW1090 | 0.39 | 195.5 | 70.3 | 75.0 | 0.7 | −3.1 |
| d-tubocurarine | 0.254 | 150.8 | 55.3 | 60.0 | 8.7 | −25.8 |
| Ex. 12 Compound | 0.227 | 128.6 | 11.9 | 15.6 | 4.9 | 7.9 |
| pancuronium | 0.013 | 169.0 | 35.6 | 45.7 | 0.2 | −1.8 |
| succinylcholine | 0.043 | 98.9 | 5.4* | 8.8* | 34.9 | 25.7 |
| RGH-4201 | 0.077 | 123.6 | 22.0 | 28.3 | 11.3 | 1.4 |
| vecuronium | 0.019 | 171.0 | 21.8 | 26.6 | 3.5 | 2.3 |

*Since cpd. is a depolarizer, data are based on twitch recovery not t-o-f.

A number of compounds in accordance with the present invention were tested for their neuromuscular blockade Properties. Specifically, the acid addition salts of the compounds were dissolved in sterile water for injection. The compounds listed in Table VI, VII and VIII below were tested by the rabbit paw twitch procedure explained above and at the indicated dose were found to have the onset and duration properties listed in the right-hand columns of Table VI, VII and VIII, except that those compounds listed as tested in mice were found to have muscle relaxant activity at a greater than 2 mg/kg dose in mice.

TABLE VI

2I$^-$

Z—N⟨piperidine⟩—C(O)(O)—C(O)(O)—⟨piperidine⟩N—Z

| No. | Z | Molecular Formula | M.W. | M.P. (°C.) | Equi. Dose | Onset (Sec) | Duration (Min.) |
|---|---|---|---|---|---|---|---|
| 1 | N-ethyl, N-CH$_2$CO$_2$CH$_2$CH$_3$ on methylcyclohexenyl | C$_{43}$H$_{70}$N$_4$O$_8$I$_2$·2H$_2$O | 1060.88 | 85–90 (foam) | 0.408 | 39.0 | 11.5 |
| 2 | trimethoxy piperidinyl methylcyclohexenyl | C$_{47}$H$_{78}$N$_4$O$_{10}$I$_2$·2H$_2$O | 1148.99 | 120–125 (dec) | | Tested in Mice | |

TABLE VI-continued

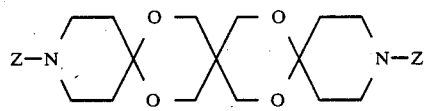

2I⁻

| No. | Z | Molecular Formula | M.W. | M.P. (°C.) | Equi. Dose | Onset (Sec) | Duration (Min.) |
|---|---|---|---|---|---|---|---|
| 3 | (cyclopropylmethyl-ethyl-trimethylcyclohexenyl-N⁺) | $C_{43}H_{70}N_4O_4I_2 2H_2O$ | 978.87 | 140–145 (foam) | 0.178 | 52.5 | 7.7 |
| 4 | (dimethoxy-hydroxy-piperidinyl-trimethylcyclohexenyl-N⁺) H₃CO, OCH₃, OH | $C_{45}H_{74}N_4O_{10}I_2 2H_2O$ | 1102.72 | 185–190 (soft) | | Tested in Mice | |
| 5 | (cyclopropylmethyl-methyl-trimethylcyclohexenyl-N⁺) CH₃ | $C_{41}H_{66}N_4O_4I_2 1.5H_2O$ | 961.07 | 105–107 (foam) | 0.302 | 47.6 | 11.0 |
| 6 | (dioxane-methyl-piperidinyl-trimethylcyclohexenyl-N⁺) CH₃ | $C_{41}H_{60}N_4O_8I_2 2H_2O$ | 1032.83 | 130 (dec) | 0.298 | 41.9 | 11.2 |
| 7 | (methyl-ethoxycarbonylmethyl-trimethylcyclohexenyl-N⁺) H₃C, CO₂CH₂CH₃ | $C_{41}H_{66}N_4O_4I_2$ | 932.8 | 155–100 (dec) | 0.127 | 92.2 | 10.9 |
| 8 | (azepanyl-methylcyclohexenyl-N⁺) H₃C, H | $C_{47}H_{74}N_4O_8I_2$ | 1076.9 | 160–165 (dec) | 0.523 | 44.6 | 20.0 |

TABLE VI-continued
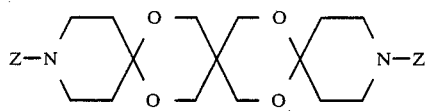
| No. | Z | Molecular Formula | M.W. | M.P. (°C.) | Equi. Dose | Onset (Sec) | Duration (Min.) |
|---|---|---|---|---|---|---|---|
| 9 | | $C_{51}H_{66}N_4O_4S_2I_2$ | 1181.12 | 135-137 | | Tested in Mice | |
| 10 | | $C_{67}H_{86}N_4O_8I_2 \cdot H_2O$ | 1347.26 | 190-193 (soft) | | Tested in Mice | |
| 11 | | $C_{51}H_{66}N_4O_8I_2$ | 1116.89 | 130-135 | 1.000 | 77.3 | 9.8 |
| 12 | | $C_{45}H_{70}N_4O_8I_2$ | 1048.83 | 142-143 (foam) | 0.322 | 40.6 | 20.1 |
| 13 | | $C_{45}H_{66}N_4O_4S_2I_2$ | 1044.93 | 160-165 (foam) | 0.238 | 88.1 | 8.3 |

TABLE VI-continued $$Z-N\underset{O}{\overset{O}{\bigcirc}}\underset{O}{\overset{O}{\bigcirc}}N-Z \cdot 2I^-$$

| No. | Z | Molecular Formula | M.W. | M.P. (°C.) | Equi. Dose | Onset (Sec) | Duration (Min.) |
|---|---|---|---|---|---|---|---|
| 14 | | $C_{47}H_{74}N_4O_8I_2 \cdot H_2O$ | 1094.99 | 110 (foam) | 0.508 | 52.8 | 25.4 |
| 15 | | $C_{51}H_{66}N_4O_6S_2I_2$ | 1149.02 | 140 (foam) | Tested in Mice | | |
| 16 | | $C_{49}H_{82}N_4O_4I_2$ | 1044.92 | 122–125 (foam) | Tested in Mice | | |
| 17 | | $C_{47}H_{74}N_4O_4I_2$ | 1012.89 | 228–231 | 1.193 | 49.6 | 8.9 |
| 18 | Ph | $C_{55}H_{78}N_4O_4I_2$ | 1130.2 | 155–160 (soft) | Tested in Mice | | |

TABLE VI-continued

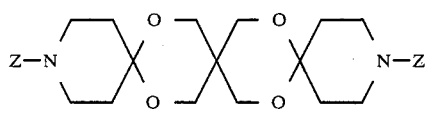

| No. | Z | Molecular Formula | M.W. | M.P. (°C.) | Equi. Dose | Onset (Sec) | Duration (Min.) |
|---|---|---|---|---|---|---|---|
| 19 | CH₃ (substituted cycloheptyl-N=cyclohexenyl) | $C_{45}H_{74}N_4O_4I_2 \cdot H_2O$ | 1000.87 | 102 (soft) | | Tested in Mice | |
| 20 | (cyclooctyl-N=cyclohexenyl) | $C_{45}H_{74}N_4O_4I_2 \cdot H_2O$ | 1000.87 | 190–194 | 0.543 | 57.5 | 8.9 |
| 21 | (cyclopropylmethyl, propyl-N=cyclohexenyl) | $C_{45}H_{74}N_4O_4I_2$ | 988.87 | 125–131 | 0.209 | 47.7 | 7.1 |
| 22 | (dibutyl-N=cyclohexenyl) | $C_{47}H_{82}N_4O_4I_2 \cdot H_2O$ | 1038.95 | 80–95 | | Tested in Mice | |
| 23 | (dipropyl-N=cyclohexenyl) | $C_{43}H_{74}N_4O_4I_2 \cdot H_2O$ | 982.85 | 95–100 (soft) | | Tested in Mice | |
| 24 | (cycloheptyl-N=cyclohexenyl) | $C_{57}H_{86}N_4S_2O_{10} \cdot 3H_2O$ (toluene sulfonate salt) | 1105.46 | 81–80 (dec.) | 0.305 | 64.0 | 7.0 |

TABLE VI-continued

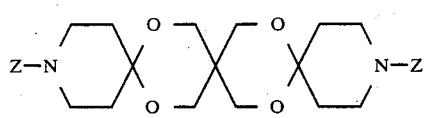
2I⁻

| No. | Z | Molecular Formula | M.W. | M.P. (°C.) | Equi. Dose | Onset (Sec) | Duration (Min.) |
|---|---|---|---|---|---|---|---|
| 25 | Ph, N–Et (C=O), piperidinium, 3,5-dimethylcyclohexenyl | $C_{59}H_{84}N_6O_6I_2$ | 1203.13 | 170–173 | | Tested in Mice | |
| 26 | CH₂Ph, piperidinium, 3,5-dimethylcyclohexenyl | $C_{56}H_{78}N_4O_4I_2$ | 1113.02 | 129–134 | | Tested in Mice | |
| 27 | 3,5-dimethylpiperidinium, 3,5-dimethylcyclohexenyl | $C_{45}H_{74}N_4O_4I_2$ | 988.89 | 137–142 | | Tested in Mice | |
| 28 | 4-methylpiperidinium, 3,5-dimethylcyclohexenyl | $C_{43}H_{70}N_4O_4I_2$ | 960.84 | 177–180 | 0.459 | 49.9 | 8.5 |
| 29 | azepanium, 3,5-dimethylcyclohexenyl | $C_{43}H_{70}N_4O_4I_2$ | 960.84 | 165–170 | 0.241 | 56.1 | 6.59 |

TABLE VI-continued
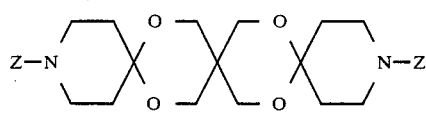
2I⁻
| No. | Z | Molecular Formula | M.W. | M.P. (°C.) | Equi. Dose | Onset (Sec) | Duration (Min.) |
|---|---|---|---|---|---|---|---|
| 30 | CO₂CH₂CH₃ (piperazine-cyclohexenyl) | $C_{45}H_{72}N_6O_8I_2$ | 1078-79 | 159-165 | Tested in Mice | | |
| 31 | Ph (piperidine-cyclohexenyl) | $C_{53}H_{74}N_4O_4I_2$ | 1085 | 158-162 | 4.260 | 105.6 | 20.3 |
| 32 | H, OH (piperidine-cyclohexenyl) | $C_{41}H_{66}N_4O_6I_2$ | 964.77 | 132-162 | Tested in Mice | | |
| 33 | CH₃ (piperidine-cyclohexenyl) | $C_{43}H_{70}N_4O_4I_2 \cdot H_2O$ | 984.67 | 120-125 | 0.153 | 53.1 | 4.9 |
| 34 | N(Et)₂-cyclohexenyl | $C_{39}H_{60}N_4O_4I_2 \cdot H_2O$ | 926.78 | 140-145 (dec) | 0.194 | 48.0 | 3.0 |
| 35 | N(allyl)₂-cyclohexenyl | $C_{43}H_{66}N_4O_4I_2$ | 956.80 | 75-80 (soft) | 0.152 | 61.9 | 6.9 |

TABLE VI-continued
2I⁻
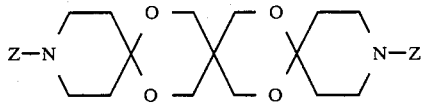
| No. | Z | Molecular Formula | M.W. | M.P. (°C.) | Equi. Dose | Onset (Sec) | Duration (Min.) |
|---|---|---|---|---|---|---|---|
| 36 | 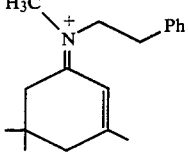 | $C_{49}H_{70}N_4O_4I_2$ | 1032.84 | 110 (soft) | 0.558 | 81.9 | 8.4 |
| 37 | 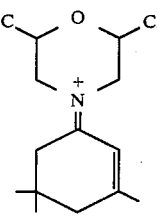 | $C_{43}H_{70}N_4O_8I_2 \cdot 2H_2O$ | 1010.82 | 181 (dec) | Tested in Mice | | |
| 38 | 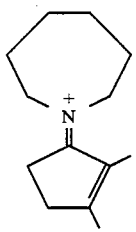 | $C_{39}H_{62}N_4O_4I_2$ | 904.72 | 197–199 | 0.146 | 100.0 | 8.0 |
| 39 | 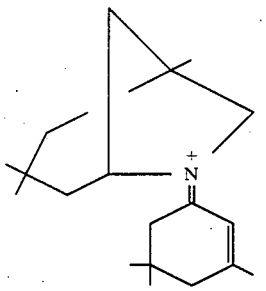 | $C_{51}H_{82}N_4O_4I_2 \cdot 2H_2O$ | 1105.05 | 193–197 | 0.150 | 75.9 | 32.8 |
| 40 | 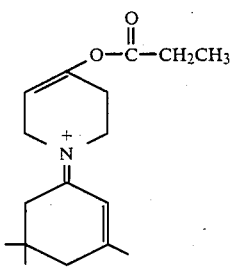 | $C_{47}H_{74}N_4O_8I_2 \cdot 2H_2O$ | 1113 | 104–107 | Tested in Mice | | |
| 41 | 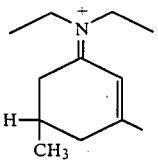 | $C_{37}H_{62}N_4O_4I_2 \cdot 2H_2O$ | 916.76 | 140–141 (foam) | 0.143 | 51.0 | 8.8 |

TABLE VI-continued
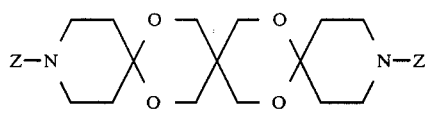
| No. | Z | Molecular Formula | M.W. | M.P. (°C.) | Equi. Dose | Onset (Sec) | Duration (Min.) |
|---|---|---|---|---|---|---|---|
| 42 | | $C_{45}H_{70}N_4O_8I_2$ | 1040.86 | 139–141 (foam) | 0.190 | 75.6 | 21.8 |
| 43 | | $C_{43}H_{70}N_4O_4I_2 \cdot \frac{1}{2}H_2O$ | 969.86 | 240–245 (dec) | 0.206 | 62.3 | 8.5 |
| 44 | | $C_{43}H_{70}N_4O_4Br_2 \cdot 2H_2O$ (bromide salt) | 866.87 | 105–110 | 0.184 | 67.2 | 6.9 |
| 45 | | $C_{47}H_{74}N_4O_8I_2$ | 1076.94 | — | Tested in Mice | | |
| 46 | | $C_{39}H_{62}N_4O_4I_2$ | 904.76 | 251–254 | 0.229 | 62.8 | 7.8 |

TABLE VI-continued

2I⁻

Z—N(...)N—Z

| No. | Z | Molecular Formula | M.W. | M.P. (°C.) | Equi. Dose | Onset (Sec) | Duration (Min.) |
|---|---|---|---|---|---|---|---|
| 47 | | $C_{45}H_{70}N_4O_8I_2$ | 1048.99 | 190–195 | Tested in Mice | | |
| 48 | | $C_{49}H_{66}N_4O_4I_2$ | 1028 | 197–199 | 1.090 | 113.5 | 12.1 |
| 49 | | $C_{39}H_{62}N_4O_6I_2$ | 936.7 | 300–304 (dec) | 1.479 | 58.8 | 22.1 |
| 50 | | $C_{41}H_{66}N_4O_4I_2$ | 932.81 | 95–100 | 1.530 | 59.9 | 24.3 |
| 51 | | $C_{43}H_{64}N_4O_4F_6I_2H_2O$ | 1086 | 135–140 (foam) | 0.302 | 51.0 | 11.5 |
| 52 | | $C_{47}H_{74}N_4O_4I_2$ | 1012.93 | 140–142 (soft) | 0.516 | 48.5 | 7.6 |

TABLE VI-continued

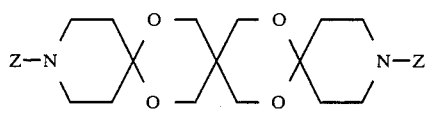

| No. | Z | Molecular Formula | M.W. | M.P. (°C.) | Equi. Dose | Onset (Sec) | Duration (Min.) |
|---|---|---|---|---|---|---|---|
| 53 | (ethyl, propyl-dioxolane substituent) | $C_{45}H_{74}N_4O_8I_2$ | 1052.89 | 100–105 (soft) | 0.120 | 58.6 | 12.6 |
| 54 | (diethyl substituent) | $C_{37}H_{62}N_4O_4I_2 \cdot 2H_2O$ | 916.7 | 140–141 (foam) | 0.143 | 51.0 | 8.8 |
| 55 | (spiro dioxolane azepanium substituent) | $C_{45}H_{70}N_4O_8I_2$ | 1040.86 | 139–141 | 0.190 | 75.6 | 21.8 |
| 56 | (cyclopropylmethyl, propyl substituent) | $C_{43}H_{70}N_4O_4I_2 \cdot \tfrac{1}{2}H_2O$ | 969.8 | 240–245 | 0.206 | 62.3 | 8.5 |
| 57 | (spiro dioxolane piperidinium substituent) | $C_{43}H_{66}N_4O_8I_2 \cdot H_2O$ | 1038.89 | 180–192 | Tested in Mice | | |
| 58 | (cyclopropylmethyl, methoxyethyl substituent) | $C_{43}H_{70}N_4O_6I_2S_2 \cdot H_2O$ | 1001.86 | 190–95 | 0.132 | 50.0 | 12.68 |

TABLE VII

[Structure: bis-spiro piperidinium diiodide with two Z-N groups, 2I⁻ counterions]

| No. | Z | Molecular Formula | M.W. | M.P. (°C.) | Equi. Dose | Onset (Sec) | Duration (Min.) |
|---|---|---|---|---|---|---|---|
| 1 | [3,5,5-trimethylcyclohex-2-enylidene piperidinium with H₃CO, OCH₃, OCH₃ substituents] | $C_{47}H_{78}N_4O_{10}I_2$ | 1112.96 | 165–170 (foam) | 0.705 | 44.4 | 18.8 |
| 2 | [N-cyclopropylmethyl, N-ethyl, 3,5,5-trimethylcyclohex-2-enylidene] | $C_{43}H_{70}N_4O_4I_2$ | 960.86 | 135–140 (soft) | 0.247 | 39.3 | 7.3 |
| 3 | [N-cyclopropylmethyl, N-methyl, 3,5,5-trimethylcyclohex-2-enylidene] | $C_{41}H_{66}N_4O_4I_2 \cdot 2H_2O$ | 950.82 | 155–158 (foam) | 0.374 | 40.1 | 7.3 |
| 4 | [dioxane-fused methylpiperidinium with cyclohexenylidene] | $C_{47}H_{74}N_4O_8I_2 \cdot H_2O$ | 1094.94 | 175–180 | 0.568 | 36.7 | 12.3 |
| 5 | [N-cyclopropylmethyl, N-propyl, 3,5,5-trimethylcyclohex-2-enylidene] | $C_{45}H_{74}N_4O_4I_2$ | 988.88 | 125–130 (foam) | 0.319 | 41.4 | 10.9 |
| 6 | [N-ethyl, N-(thien-2-ylmethyl), 3,5,5-trimethylcyclohex-2-enylidene] | $C_{45}H_{66}N_4O_4S_2I_2$ | 1044.97 | 145–149 | 0.484 | 55.0 | 10.0 |

TABLE VII-continued

| No. | Z | Molecular Formula | M.W. | M.P. (°C.) | Equi. Dose | Onset (Sec) | Duration (Min.) |
|---|---|---|---|---|---|---|---|
| 7 | (azepanyl-methylcyclohexenyl) | $C_{41}H_{66}N_4O_4 I_2$ | 932.88 | 170–172 | 0.084 | 75.6 | 10.0 |
| 8 | $H_3C$–N($CO_2CH_2CH_3$)– | $C_{41}H_{66}N_4O_8 I_2 \cdot 3H_2O$ | 976.81 | 147–151 (soft) | 0.958 | 33.9 | 9.7 |
| 9 | diethyl-N (methoxycyclohexenyl) | $C_{38}H_{66}N_4O_4 I_2$ | 896.75 | 150–154 (foam) | 0.324 | 40.2 | 6.6 |
| 10 | (dioxaspiro piperidinyl) | $C_{45}H_{70}N_4O_8 I_2$ | 1048.89 | 175–180 (dec) | 0.490 | 40.8 | 11.2 |
| 11 | (difurfuryl/thienyl-N) | $C_{51}H_{66}N_4O_6S_2 I_2$ | 1149.01 | 130–150 (foam) | Tested in Mice | | |
| 12 | (methyl-azepanyl) | $C_{59}H_{88}N_4O_{10}S_2 \cdot H_2O$ | 1113.44 | 85–91 | 0.657 | 50.8 | 10.6 |

TABLE VII-continued

| No. | Z | Molecular Formula | M.W. | M.P. (°C.) | Equi. Dose | Onset (Sec) | Duration (Min.) |
|---|---|---|---|---|---|---|---|
| 13 | | $C_{47}H_{74}N_4O_8 I_2 H_2O$ | 1112.91 | 188–192 (foam) | 0.274 | 36.5 | 12.7 |
| 14 | | $C_{69}H_{92}N_4O_{10}S_2 \cdot 2H_2O$ | 1233.56 | 126–128 | | Tested in Mice | |
| 15 | | $C_{57}H_{86}N_4S_2O_{10} \cdot 2H_2O$ (toluene sulfonate salt) | 1087.42 | 68–72 (soft) | 0.147 | 57.9 | 8.3 |
| 16 | | $C_{47}H_{74}N_4O_4 I_2 H_2O$ | 1030.90 | 120–122 (dec) | 0.494 | 42.2 | 8.8 |
| 17 | | $C_{43}H_{70}N_4O_4 I_2$ | 960.86 | 135–140 (soft) | 0.247 | 39.3 | 7.3 |
| 18 | | $C_{47}H_{78}N_4O_{10} I_2$ | 1112.96 | 165–170 | 0.705 | 44.4 | 18.8 |

TABLE VII-continued

| No. | Z | Molecular Formula | M.W. | M.P. (°C.) | Equi. Dose | Onset (Sec) | Duration (Min.) |
|---|---|---|---|---|---|---|---|
| 19 | H₃CO, OCH₃, OH | C₄₅H₇₄N₄O₁₀I₂ · 1.5H₂O | 1086.92 | 170–175 | 1.604 | 53.2 | 25.9 |
| 20 | CH₃ | C₄₃H₇₀N₄O₄I₂ · H₂O | 978.88 | 162–167 | 0.324 | 44.9 | 8.0 |
| 21 | (ethyl, propyl dioxolane) | C₄₅H₇₄N₄O₈I₂ · H₂O | 1070.92 | 110–115 | 0.605 | 33.3 | 11.8 |
| 22 | (dicyclopropylmethyl) | C₄₇H₇₄N₄O₄I₂ · H₂O | 1030.93 | 120–122 (dec) | 0.494 | 42.2 | 8.8 |

TABLE VIII

| No. | Z | Molecular Formula | M.W. | M.P. (°C.) | Equi. Dose | Onset (Sec) | Duration (Min.) |
|---|---|---|---|---|---|---|---|
| 1 | H₃CO, OCH₃ | C₄₉H₈₂N₄O₁₀I₂ | 1141.01 | 175–180 (foam) | 0.312 | 53.4 | 21.1 |

TABLE VIII-continued

| No. | Z | Molecular Formula | M.W. | M.P. (°C.) | Equi. Dose | Onset (Sec) | Duration (Min.) |
|---|---|---|---|---|---|---|---|
| 2 | (cyclopropylmethyl-ethyl-N on 5,5-dimethylcyclohex-2-enylidene) | C₄₅H₇₄N₄O₄I₂ | 988.91 | 85–90 (foam) | 0.139 | 70.6 | 7.4 |
| 3 | (1,4-dioxaspiro piperidinium on 3-methoxy-5-methylcyclohex-2-enylidene) | C₄₅H₇₀N₄O₈I₂ | 1048.88 | 154–158 (soft) | 0.108 | 51.3 | 8 |
| 4 | (cyclopropylmethyl-ethyl-N on 5,5-dimethylcyclohex-2-enylidene) | C₄₅H₇₄N₄O₄I₂ | 988.91 | 85–90 (foam) | 0.139 | 70.6 | 7.4 |
| 5 | (trimethoxy piperidinium on 5,5-dimethyl-3-methylcyclohex-2-enylidene) | C₄₉H₈₂N₄O₁₀I₂ | 1141.01 | 175–180 (foam) | 0.312 | 53.4 | 21.1 |
| 6 | (H₃C-N⁺-CH₂CO₂CH₂CH₃ on 3-methoxycyclohex-2-enylidene) | C₄₃H₇₀N₄O₈I₂·2H₂O | 1060.88 | 133–135 (foam) | 0.146 | 52.8 | 8.7 |
| 7 | (ethyl-N⁺-CH₂CO₂CH₂CH₃ on 3-methoxycyclohex-2-enylidene) | C₄₅H₇₄N₄O₈I₂·2H₂O | 1088.94 | 125–130 (foam) | 0.231 | 43.7 | 10.1 |
| 8 | (cyclopropylmethyl-propyl-N on 5,5-dimethyl-3-methylcyclohex-2-enylidene) | C₄₇H₇₈N₄O₄I₂·H₂O | 1034.98 | 120–125 (foam) | 0.215 | 59.4 | 5.4 |

TABLE VIII-continued

[Structure: bis-spiro dioxane compound with two Z-N groups, 2I⁻ counterion]

| No. | Z | Molecular Formula | M.W. | M.P. (°C.) | Equi. Dose | Onset (Sec) | Duration (Min.) |
|---|---|---|---|---|---|---|---|
| 9 | N-cyclopropylmethyl, N-CH₂CO₂CH₂CH₃ substituted 3,3-dimethyl-5-methoxy-cyclohex-4-enylidene iminium | C₄₉H₇₈N₄O₈I₂·2H₂O | 1140.01 | 105–110 (foam) | 0.184 | 50.2 | 6.9 |
| 10 | Octahydroazocinium fused to 3-methyl-5-H-cyclohex-2-enylidene | C₄₃H₇₀N₄O₄I₂ | 960.86 | 105–110 | 0.113 | 117.3 | 12.5 |
| 11 | 1,4-Dioxa-spiro[4.5]-3-methyl-8-piperidinium linked to 3,5-dimethyl-cyclohex-2-enylidene | C₄₉H₇₈N₄O₈I₂ | 1105.0 | 174–175 | 0.166 | 62.1 | 20.6 |
| 12 | N-ethyl, N-(2-thienylmethyl) 3,3-dimethyl-5-methoxy-cyclohex-4-enylidene iminium | C₄₇H₇₀N₄O₄S₂I₂ | 1073 | 125–130 | 0.180 | 118.6 | 10.4 |
| 13 | Octahydroazocinium linked to 3,5-dimethyl-cyclohex-2-enylidene | C₄₅H₇₄N₄O₄I₂ | 988.89 | 150–157 (dec) | 0.098 | 88.3 | 8.3 |
| 14 | 1,4-Dioxa-spiro[4.5]-8-piperidinium linked to 3,5-dimethyl-cyclohex-2-enylidene | C₄₇H₇₄N₄O₈I₂ | 1076.93 | 190–195 (soft) | 0.153 | 44.5 | 10.6 |

TABLE VIII-continued

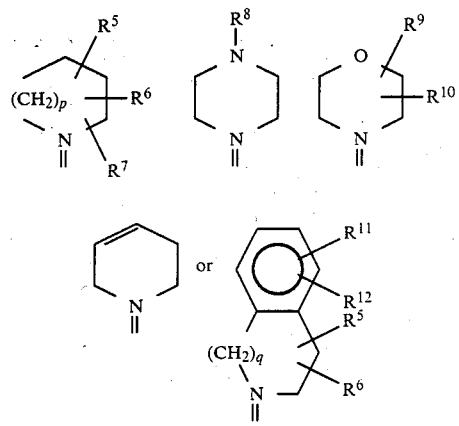

| No. | Z | Molecular Formula | M.W. | M.P. (°C.) | Equi. Dose | Onset (Sec) | Duration (Min.) |
|---|---|---|---|---|---|---|---|
| 15 | | $C_{53}H_{70}N_4O_8I_2$ | 1144.95 | 130–135 (dec) | 0.753 | 77.6 | 11.3 |
| 16 | | $C_{41}H_{71}N_4O_4I_2$ | 936.82 | 155–160 (foam) | 0.106 | 54.3 | 9.7 |

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. An enamine quaternary compound of the formula:

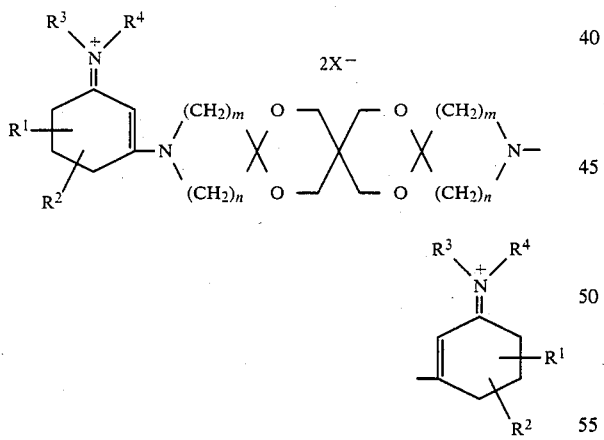

wherein m=1, 2 or 3 and n=1, 2 or 3 with the proviso that m+n=3, 4 or 5; $R^1$ and $R^2$ are independently lower alkyl or hydrogen, and $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo, or lower alkyloyloxy lower alkyl or wherein $NR^3R^4$ together comprise a heterocycle ring selected from the group consisting of wherein p is 1, 2 or 3 and q is 1 or 2 and $R^5$, $R^6$ and $R^7$, are independently hydrogen, hydroxy lower alkyl, lower alkoxy phenyl, phenyl lower alkyl wherein the phenyl is unsubstituted or substituted with up to 2 lower alkoxy groups or $R^5$ and $R^6$ combined is a lower alkyl bridge or $R^5$ and $R^6$ together are a lower ketal or lower acetal moiety; $R^8$ is lower alkyl or diphenylmethylene wherein the phenyl may be unsubstituted or substituted by a halogen; $R^9$ and $R^{10}$ are independently selected from lower alkyl $R^{11}$ hydrogen; and $R^{12}$ are on the same or different carbons and independently are hydrogen, lower alkyl or lower alkoxy, and wherein X- is a pharmaceutically acceptable anion.

2. An enamine quaternary compound of the formula:

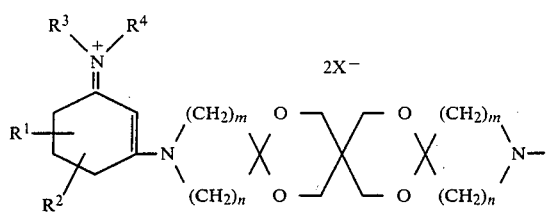

wherein m = 1, 2 or 3 and n = 1, 2 or 3 with the proviso that m+n 3, 4 or 5; $R^1$ and $R^2$ are independently lower alkyl or hydrogen, and $R^3$ and $R^4$ are independently selected from the group consisting of lower alkyl, cyclo lower alkyl, lower alkenyl, phenyl lower alkyl, thienyl lower alkyl, furyl lower alkyl, lower alkoxy lower alkyl halogenated lower alkyl, lower alkyloyloxo, or lower alkyloyloxy lower alkyl and wherein X- is a pharmaceutically acceptable anion.

3. An enamine quaternary compound of the formula:

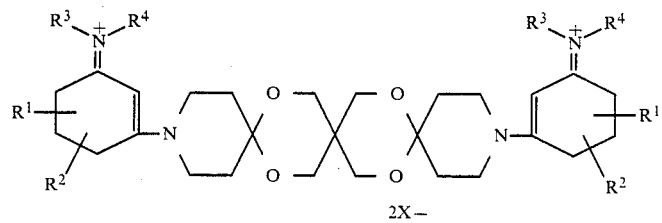

wherein $R^1$ and $R^2$ are independently lower alkyl or hydrogen, and $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl halogenated lower alkyl, lower alkyloyloxo, or lower alkyloyloxy lower alkyl and wherein X- is a pharmaceutically acceptable anion.

4. A compound of claim 1, wherein $R^3$ is lower cycloalkyl lower alkyl and $R^4$ is lower alkyl, fluorinated lower alkyl or lower alkoxy lower alkyl.

5. A compound of claim 1, consisting of

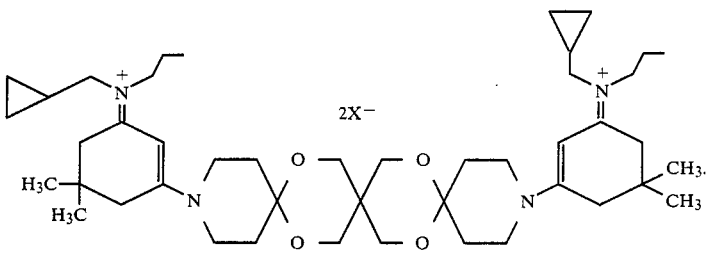

6. A compound of claim 1, consisting of

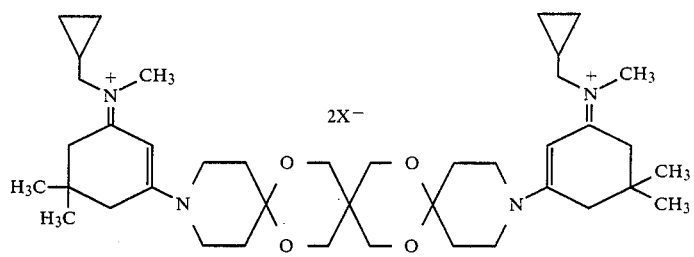

7. The enamine quaternary compound of claim 1 wherein X- is selected from halides, sulfates, methane sulfonate, benzene sulfonate, nitrobenzene sulfonate, toluene sulfonate and naphthalene sulfonate.

8. A muscle relaxant composition comprising a muscle relaxing effective amount of an enamine quaternary compound of the formula:

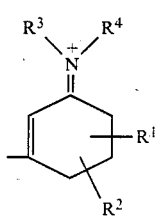 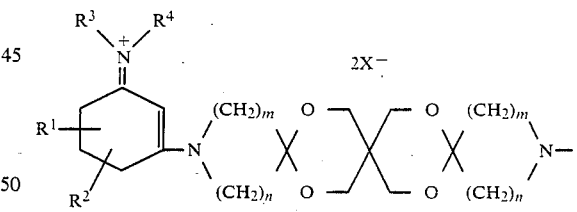

-continued

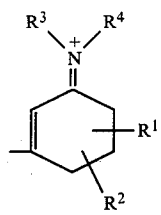

wherein m=1, 2 or 3 and n=1, 2 or 3 with the proviso that m+n=3, 4 or 5; $R^1$ and $R^2$ are independently lower alkyl or hydrogen, and $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkyloyloxy lower alkyl or wherein $NR^3R^4$ together comprise a heterocycle ring selected from the group consisting of

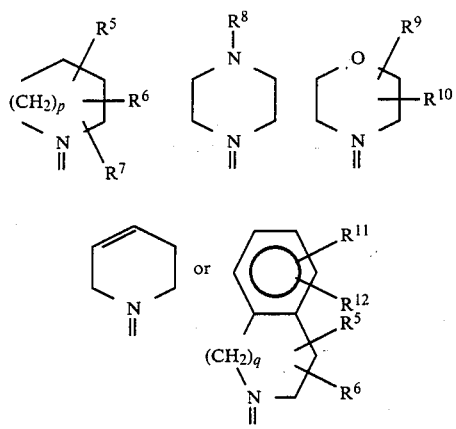

wherein P is 1, 2 or 3 and q is 1 or 2, $R^5$, $R^6$, and $R^7$ are independently hydrogen, hydroxy lower alkyl, lower alkoxy phenyl, phenyl lower alkyl wherein the phenyl is unsubstituted or substituted with up to 2 lower alkoxy groups or $R^5$ and $R^6$ combined is a lower alkyl bridge or $R^5$ and $R^6$ together are a lower ketal or lower acetal moiety; $R^8$ is lower alkyl or diphenylmethylene wherein the phenyl may be unsubstituted or substituted by a halogen; $R^9$ and $R^{10}$ are independently selected from lower alkyl and hydrogen; $R^{11}$ and $R^{12}$ are on the same or different carbons and independently are hydrogen, lower alkyl or lower alkoxy; and wherein $X^-$ represents a pharmaceutically acceptable anion; and a pharmaceutically acceptable carrier.

9. A muscle relaxant composition comprising a muscle relaxing effective amount of an enamine quaternary compound of the formula:

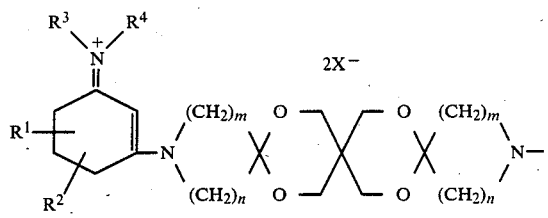

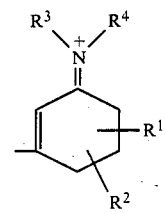

wherein m=1, 2 or 3 and n=1, 2 or 3 with the proviso that m+n 3, 4 or 5; $R^1$ and $R^2$ are independently lower alkyl or hydrogen, and $R^3$ and $R^4$ are independently selected from the group consisting of lower alkyl, lower cycloalkyl lower alkyl, lower alkylene, phenyl lower alkyl, thienyl lower alkyl, furyl lower alkyl, lower alkoxy lower alkyl, halogenated lower alkyl, lower alkyloyloxo or lower alkyloyloxy lower alkyl and wherein $X^-$ represents a pharmaceutically acceptable anion; and a pharmaceutically acceptable carrier.

10. A muscle relaxant composition comprising a muscle relaxing effective amount of an enamine quaternary compound of the formula:

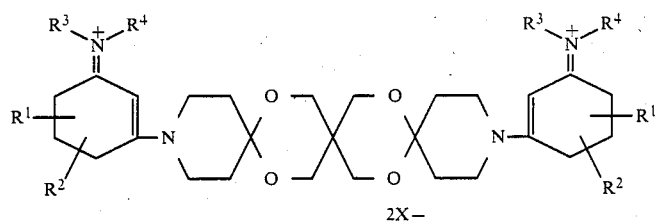

wherein $R^1$ and $R^2$ are independently lower alkyl or hydrogen, and $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkyloyloxy lower alkyl and wherein $X^-$ represents a pharmaceutically acceptable anion; and a acceptable carrier.

11. A composition of claim 8, wherein $R^3$ is lower cycloalkyl lower alkyl and $R^4$ is lower alkyl, fluorinated lower alkyl or lower alkoxy lower alkyl.

12. A composition of claim 8, consisting of a muscle relaxing effective amount of

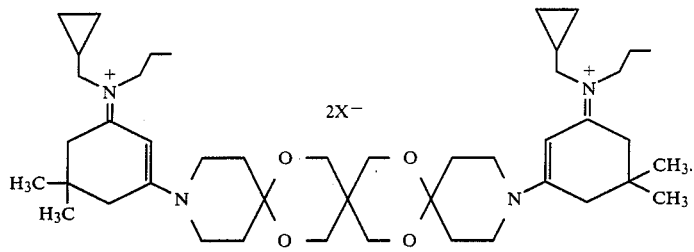

13. A composition of claim 8, consisting of a muscle relaxing effective amount of

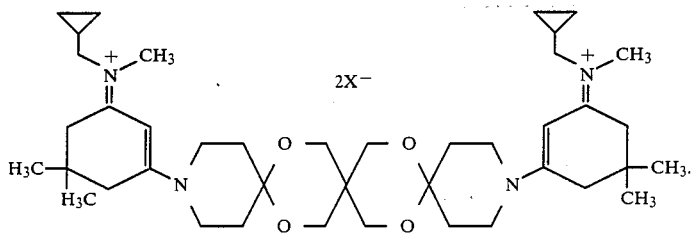

14. The composition of claim 8, wherein the carrier is distilled water or saline solution.

15. The composition of claim 8, wherein $X^-$ is selected from halides, sulfates, methane sulfonate, benzene sulfonate, nitrobenzene sulfonate, toluene sulfonate and naphthalene sulfonate.

16. The composition of claim 8, wherein the muscle relaxing effective amount of said compound is in range of from about 0.1 mg/kg to about 7.0 mg/kg.

17. The composition of claim 8, wherein the muscle relaxing effective amount of said compound is in the range of from about 0.15 mg/kg to about 2.5 mg/kg.

18. A method of attaining a muscle relaxing effect in a warm-blooded animal comprising administering to said warm-blooded animal by intravenous injection a muscle relaxing effective amount of a pharmaceutical composition comprising an enamine quaternary compound of the formula

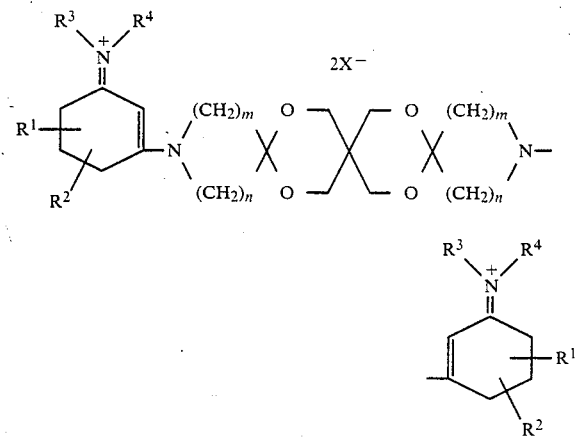

wherein $m=1$, 2 or 3 and $n=1$, 2 or 3 with the proviso that $m+n=3$, 4 or 5; $R^1$ and $R^2$ are independently lower alkyl or hydrogen, and $R^3$ and $R^4$ are independently selected from the group consisting of lower alkyl, lower cycloalkyl lower alkyl, lower alkenyl, phenyl lower alkyl, thienyl lower alkyl, furyl lower alkyl, lower alkoxy lower alkyl, halogenated lower alkyl, lower alkyloyloxo or lower alkyloyloxy lower alkyl or wherein $NR^3R^4$ together comprise a heterocycle ring selected from the group consisting of

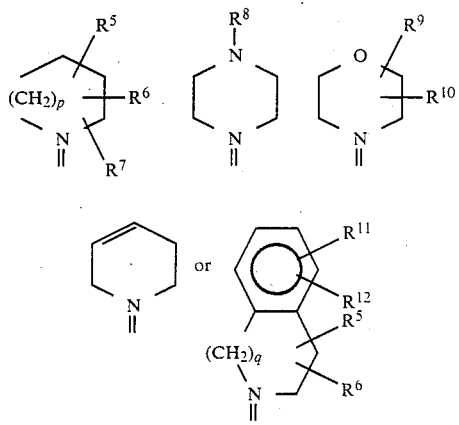

wherein p is 1, 2 or 3 and q is 1 or 2, $R^5$, $R^6$, and $R^7$ are independently hydrogen hydroxy lower alkyl, lower alkoxy phenyl, phenyl lower alkyl wherein the phenyl is unsubstituted or substituted with up to 2 lower alkoxy groups or $R^5$ and $R^6$ combined is a lower alkyl bridge or $R^5$ and $R^6$ together are a lower ketal or lower acetal moiety; $R^8$ is lower alkyl or diphenylmethylene wherein the phenyl may be unsubstituted or substituted by a halogen; $R^9$ and $R^{10}$ are independently selected from lower alkyl and hydrogen; $R^{11}$ and $R^{12}$ are on the same or different carbons and independently are hydrogen, lower alkyl or lower alkoxy; and wherein $X^-$ represents a pharmaceutically acceptable anion; and a pharmaceutically acceptable carrier.

19. A method of attaining a muscle relaxing effect in a warm-blooded animal comprising administering to said warm-blooded animal by intravenous injection a muscle relaxing effective amount of a pharmaceutical composition comprising an enamine quaternary compound of the formula

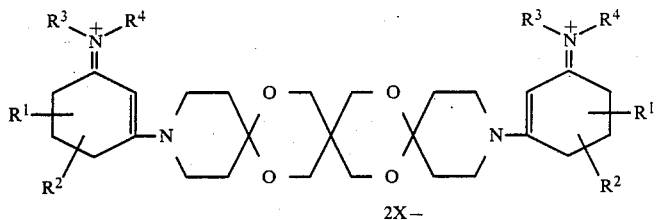

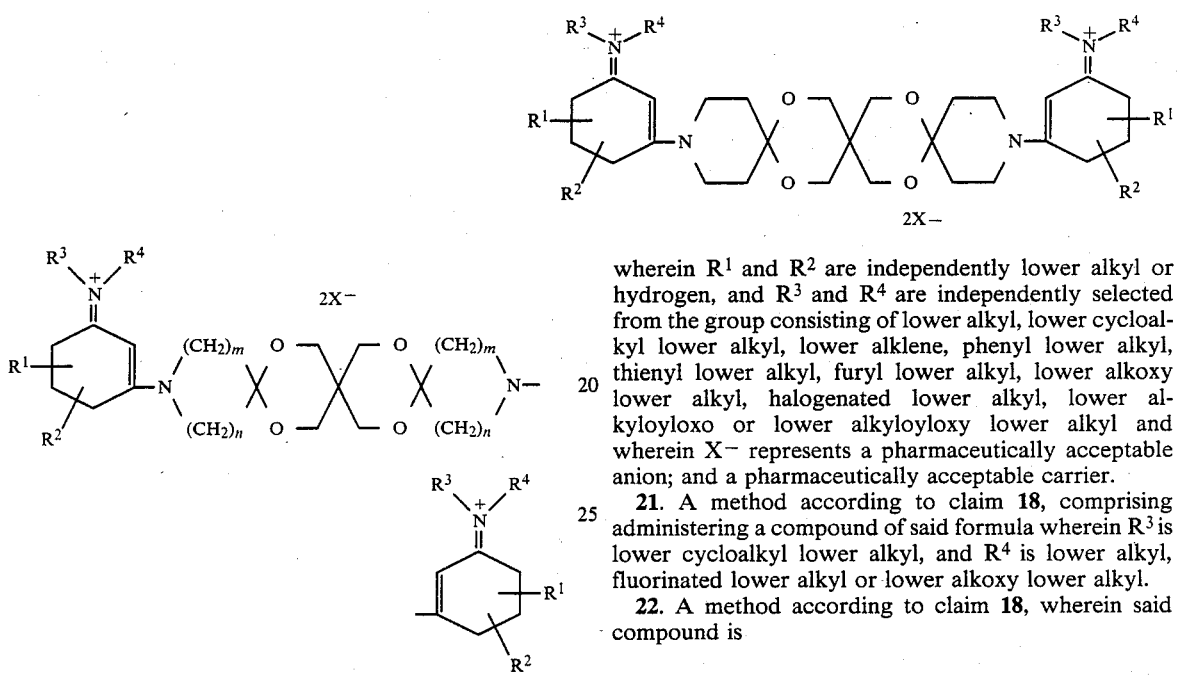

wherein m=1, 2 or 3 and n=1, 2 or 3 with the proviso that m+n=3, 4 or 5; $R^1$ and $R^2$ are independently lower alkyl or hydrogen, and $R^3$ and $R^4$ are independently selected from the group consisting of lower alkyl, lower cycloalkyl lower alkyl, lower alklene, phenyl lower alkyl, thienyl lower alkyl, furyl lower alkyl, lower alkoxy lower alkyl, halogenated lower alkyl, lower alkyloyloxo or lower alkyloyloxy lower alkyl and wherein $X^-$ represents a pharmaceutically acceptable anion; and a pharmaceutically acceptable carrier.

20. A method of attaining a muscle relaxing effect in a warm-blooded animal comprising administering to said warm-blooded animal by intravenous injection a muscle relaxing effective amount of a pharmaceutical composition comprising an enamine quaternary compound of the formula wherein $R^1$ and $R^2$ are independently lower alkyl or hydrogen, and $R^3$ and $R^4$ are independently selected from the group consisting of lower alkyl, lower cycloalkyl lower alkyl, lower alklene, phenyl lower alkyl, thienyl lower alkyl, furyl lower alkyl, lower alkoxy lower alkyl, halogenated lower alkyl, lower alkyloyloxo or lower alkyloyloxy lower alkyl and wherein $X^-$ represents a pharmaceutically acceptable anion; and a pharmaceutically acceptable carrier.

21. A method according to claim 18, comprising administering a compound of said formula wherein $R^3$ is lower cycloalkyl lower alkyl, and $R^4$ is lower alkyl, fluorinated lower alkyl or lower alkoxy lower alkyl.

22. A method according to claim 18, wherein said compound is

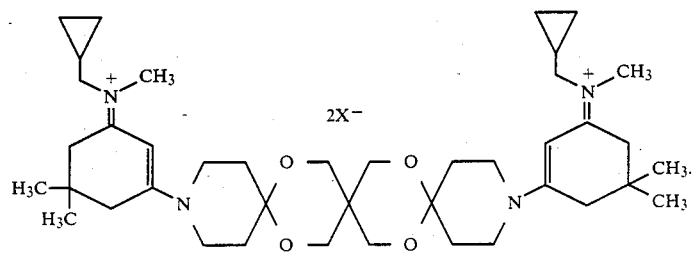

23. A method according to claim 18, wherein said compound is

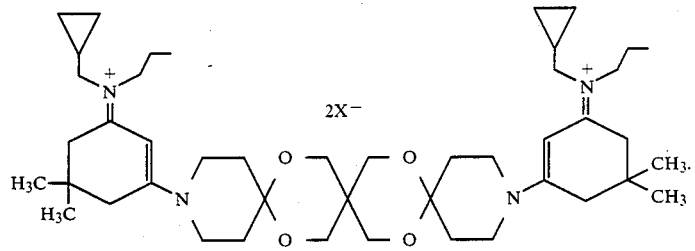

24. The method of claim 18, wherein the carrier is distilled water or a saline solution.

25. The method of claim 18, wherein $X^-$ is selected from halides, sulfates, methane sulfonate, benzene sulfonate, nitrobenzene sulfonate, toluene sulfonate and naphthalene sulfonate.

26. The method of claim 18, wherein the muscle relaxing effective amount of the enamine quaternary compound is from about 0.1 mg/kg to about 7.0 mg/kg.

27. The method of claim 26, wherein the muscle relaxing effective amount of the enamine quaternary compound is in the range from 0.15 mg/kg to about 2.5 mg/kg.

28. A method of producing a enamine quaternary compound of the formula

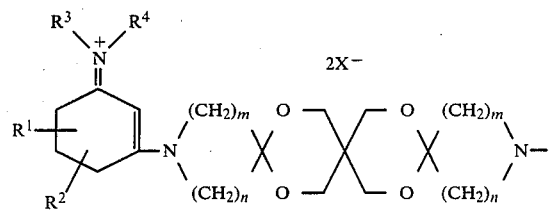

wherein m=1, 2 or 3 and n=1, 2 or 3 with the proviso that m+n=3, 4 or 5; $R^1$ and $R^5$ are independently lower alkyl or hydrogen, and $R^3$ and $R^4$ are independently selected from the group consisting of lower alkyl, lower cycloalkyl lower alkyl, lower alkylene, phenyl lower alkyl, thienyl lower alkyl, furyl lower alkyl, lower alkoxy lower alkyl, halogenated lower alkyl, lower alkyloyloxo or lower alkyloyloxy lower alkyl or wherein $NR^3R^4$ together comprise a heterocycle ring selected from the group consisting of

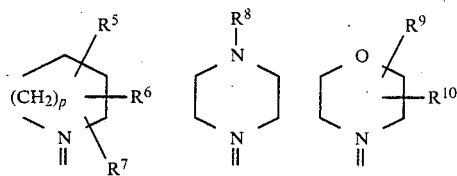

-continued

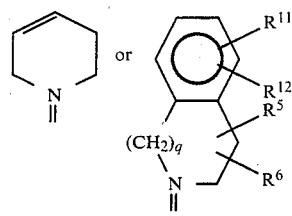

wherein p is 2 or 3, q is 1 or 2, and $R^5$, $R^6$ and $R^7$ are independently hydrogen, hydroxy lower alkyl, lower alkoxy phenyl, phenyl lower alkyl wherein the phenyl is unsubstituted or substituted with up to 2 lower alkoxy groups or $R^5$ and $R^6$ combined is a lower alkyl bridge or $R^5$ and $R^6$ together are a lower ketal or lower acetal moiety; $R^8$ is lower alkyl or diphenylmethylene wherein the phenyl may be unsubstituted or substituted by a halogen; $R^9$ and $R^{10}$ are independently selected from lower alkyl and hydrogen; $R^{11}$ and $R^{12}$ are on the same or different carbons and independently are hydrogen, lower alkyl or lower alkoxy, and wherein Xhu — represents a pharmaceutically acceptable anion; comprising:

(a) reacting a compound of the formula

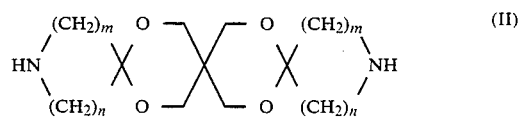 (II)

with a compound of the formula

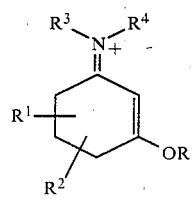

where R is selected from the group consisting of lower alkyl, mesyl and triflate groups and m, n, $R^1$, $R^2$, $R^3$ and $R^4$ are as defined above and $X^-$ represents a pharmaceutically acceptable anion, in the presence of an organic solvent in the presence of a base at ambient temperature.

29. The method of claim 28, wherein the R group is methyl.

30. The method of claim 28, wherein the organic solvent is methanol.

* * * * *